United States Patent [19]
De Block

[11] Patent Number: 6,074,876
[45] Date of Patent: Jun. 13, 2000

[54] GENETIC TRANSFORMATION USING A PARP INHIBITOR

[75] Inventor: Marc De Block, Merelbeke, Belgium

[73] Assignee: Plant Genetic Systems, N.V., Ghent, Belgium

[21] Appl. No.: 08/817,188

[22] PCT Filed: Jul. 31, 1996

[86] PCT No.: PCT/EP96/03366

§ 371 Date: May 15, 1997

§ 102(e) Date: May 15, 1997

[87] PCT Pub. No.: WO97/06267

PCT Pub. Date: Feb. 20, 1997

[30] Foreign Application Priority Data

Aug. 4, 1995 [EP] European Pat. Off. .............. 95401844

[51] Int. Cl.$^7$ ........................... C12N 15/82; C12N 15/84; C12N 15/55; A01H 1/02

[52] U.S. Cl. .................... 435/468; 435/199; 435/418; 435/419; 435/420; 435/430; 435/469; 800/278; 800/287; 800/294; 800/300; 800/303; 800/306; 800/320; 800/320.3

[58] Field of Search ..................................... 800/205, 278, 800/294, 287, 303, 320.3, 300, 320, 306; 435/199, 468, 469, 418, 419, 430, 420

[56] References Cited

FOREIGN PATENT DOCUMENTS

A1 424047 10/1990 European Pat. Off. .
0 424 047 A1 4/1991 European Pat. Off. .

OTHER PUBLICATIONS

"Illegitimate and homologous recombination in mammalian cells: differential sensitivity to an inhibitor of poly(ADP–ribosylation)" by B. C. Waldman et al., Nucleic Acids Research, vol. 18, No. 20 (1990) pp. 5981–5988.

"Secondary Metabolism In Cultured Red Beet Beta–Vugaris L. Cells Differential Regulation of Betaxanthin and Betacyanin Biosynthesis" by P–A Girod et al, Biological Abstracts, vol. 92 (1991), Abstract No. 16692.

"Reduced Position Effect in Mature Transgenic Plants Conferred by the Chicken Lysozyme Matrix–Associated Region" by L. Mlynarova et al, The Plant Cell, vol. 6 (1994) pp. 417–426.

"Scaffold Attachment Regions Increase Reporter Gene Expression in Stably Transformed Plant Cells" by G. C. Allen et al, The Plant Cell, vol. 5 (1993) pp. 603–613.

"Transgene expression variability (position effect) of CAT and GUS reporter genes driven by linked divergent T–DNA promoters" by C. Peach et al, Plant Molecular Biology, vol. 17 (1991) pp. 49–60.

"In vivo random beta–glucuronidase gene fusions in *Arabidopsis thaliana*" by S. Kertbundit et al, Proceedings of the National Academy of Sciences of USA, vol. 88 (1991) pp. 5212–5216.

"Assessment of promoter trap as a tool to study zygotic embryogenesis in *Arabidopsis thaliana*" by M. Devic et al, Compes Rendus De L'Academie Des Sciences Serie III Sciences De La Vie. 318 (1) (1995), pp. 121–128.

"Identification of *Arabidopsis thaliana* sequences responsive to low temperature and abscisic acid by T–DNA tagging and in–vivo gene fusion" by A. Mandal et al, Chemical Abstracts, vol. 123, No. 21, (1995), Abstract No. 276968.

Waldman et al. Illegitimate and homologous recombination in mammalian cells: differential sensitivity to an inhibitor of poly (ADP–ribosylation). Nucleic Acids Research. 18(20):5981–5988, 1988.

Strain. Inhibitors of ADP–ribosyl transferase enhance the transformation of NIH3T3 cells following transfection with SV40 DNA. Exp. Cell Res. 159:531–535, Aug. 1985.

*Primary Examiner*—David T. Fox
*Attorney, Agent, or Firm*—Birch, Stewart, Kolasch & Birch, LLP

[57] ABSTRACT

The invention concerns a process for producing transgenic plant cells, which comprises: contacting a culture of plant cells with an inhibitor of poly-(ADP-ribose) polymerase, prior to transformation, for a period of time sufficient to reduce the response of the cultured cells to stress and to reduce their metabolism. The untransformed cells are then contacted with foreign DNA comprising at least one gene of interest under conditions in which the foreign DNA is taken up by the untransformed cells and the gene of interest is stably integrated in the nuclear genome of the untransformed cells to produce the transgenic cells. The transgenic plant cells are recovered from the culture.

The invention further concerns a process for increasing the frequency of obtaining transgenic plant cells, via Agrobacterium-mediated transformation, which comprises: contacting a culture of plant cells with an inhibitor or poly(ADP-ribose) polymerase prior to transformation for a period of approximately 1 to 2 days or culturing transgenic plant cells after transfomation in a medium containing an inhibitor of poly (ADP-ribose) polymerase for a period of time of approximately 1 to 14 days.

35 Claims, No Drawings

GENETIC TRANSFORMATION USING A PARP INHIBITOR

FIELD OF THE INVENTION

This invention is related to tissue culture of eucaryotic cells and improved techniques to obtain genetically transformed eucaryotic cells and organisms, such as transgenic plant cells or plants, by lowering the stress reaction of cultured eucaryotic cells prior to contacting the cells with foreign DNA, particularly by specific inhibition of poly-(ADP-ribose) polymerase.

BACKGROUND OF THE INVENTION

Over the years many techniques for the genetic transformation of higher organisms (animals and plants) have been developed. In these techniques it is the ultimate goal to obtain a transgenic organism, e.g. a plant, in which all cells contain a foreign DNA comprising a gene of interest (the so-called transgene) stably integrated in their genome, particularly their nuclear genome.

Transformation is a complex process which always involves the contacting of starting cells with a DNA, usually a DNA comprising foreign gene(s) of interest. The contacting of the cells with the DNA is carried out under conditions that promote the uptake of the DNA by the cells and the integration of the DNA, including the gene(s) of interest into the genome of the cell.

Starting cells for transformation are usually cells that have been cultured in vitro for some time. After contacting the cells with the DNA, the transformed cells generally need to be cultured in vitro for a certain period in order to separate the transformed cells from the non-transformed cells and, in the case of plants, to regenerate transformed plants from the transformed cells. Indeed, complete plants can be regenerated from individual transformed cells thus ensuring that all cells of the regenerated plant will contain the transgene.

In many plants, genetic transformation can be achieved by using the natural capacity of certain Agrobacterium strains to introduce a part of their Ti-plasmid, i.e. the T-DNA, into plant cells and to integrate this T-DNA into the nuclear genome of the cells. It was found that the part of the Ti-plasmid that is transferred and integrated is delineated by specific DNA sequences, the so-called left and right T-DNA border sequences and that the natural T-DNA sequences between these border sequences can be replaced by foreign DNA (European Patent Publication "EP" 116718; Deblaere et al, 1987 Meth.Enzymol. 153:277–293).

Certain plant species have proven to be recalcitrant to Aqrobacterium mediated transformation and in these species, as well as in animals, genetic transformation has been achieved by means of direct gene transfer by which DNA is inserted into the cells by physical and/or chemical means, such as by electroporation, by treatment of the cells with polyethyleneglycol (PEG), by bombardment of the cells with DNA-coated microprojectiles, etc. (WO 92/09696; Potrykus et al, 1991, Annu.Rev.Plant Physiol-.Plant Mol.Biol. 42:205–225).

Genetic transformation of eucaryotic cells is generally a random event, i.e. the transgene is integrated in the genome at random positions. Often several copies (or parts of copies) of the transforming DNA are integrated in a single position, and/or at different positions, resulting in a transformed cell containing multiple copies of the transgene.

The expression of the transgene is known to be influenced by its position in the genome. For instance, a foreign DNA, when introduced in a plant cell appears to integrate randomly in the plant genome. Examination of independently transformed plants has shown a high degree of variability (up to 1 00-fold) in the expression level of the introduced gene. Several studies have shown no correlation between this "between-transformant variability" and the copy number of the introduced DNA at a given locus. It has been suggested that some of the variability in expression of introduced genes in transgenic plants is a consequence of "position effects" caused by influences of adjacent plant genomic DNA. Other factors that could contribute to the variability in expression are physiological variability of the plant material, differences in the number of independent T-DNA loci in different transformants or the inhibitory effects of certain T-DNA structures on gene expression. Between-transformant variability in expression has been observed for the majority of introduced genes in transgenic plants. The variability in expression of many introduced genes in independent transgenic plants necessitates large numbers of transgenic plants to be assayed to accurately quantitate the expression of the gene. It would be of great importance if the amount of between-transformant variability could be reduced (Dean et al, 1988, NAR 16:9267-9283).

If the transgene is under the control of a tissue-specific promoter, with the expectation that it will be expressed in selected tissues of the transformed organisms, the position effects can lead, at least in some transformants, to loss of specificity of the promoter and expression of the transgene in undesired tissues, e.g. in tissue cultured in vitro.

Factors that are known to influence the efficiency and quality of the genetic transformation process are the method of DNA delivery, specific tissue culture conditions, the physiological and metabolic state of the target cells etc. Direct gene transfer methods for instance are generally known to result in transformed organisms with a high copy number of the transgene. Many of these factors are not under the control of man.

SUMMARY OF THE INVENTION

This invention provides a process for producing transgenic eucaryotic cells, particularly plant cells. The process comprises contacting a culture of untransformed cells with an inhibitor of poly-(ADP-ribose) for a period of time sufficient to reduce the response of the cultured cells to stress and to reduce the metabolism of the cultured cells, particularly to reduce the electron flow in the mitochondrial electron transport chain. The untransformed cells are then contacted with foreign DNA comprising at least one gene of interest under conditions in which the foreign DNA is taken up by the untransformed cells and the gene of interest is stably integrated in the nuclear genome of the untransformed cells to produce the transgenic cells which are recovered from the culture.

The process may preferably comprise contacting untransformed eucaryotic (e.g.) cells with foreign DNA comprising at least one gene of interest under conditions in which the foreign DNA is taken up by the untransformed cells and the gene of interest is stably integrated in the nuclear genome of the untransformed cells to produce the transgenic cells. The untransformed cells are cultured in vitro in a culture medium containing an inhibitor of poly-(ADP-ribose) polymerase, preferably niacinamide, preferably for at least 2 to 3 days, particularly for at least 4 days (e.g. 4–5 days), before the contacting of the untransformed cells with the foreign DNA. The inhibitor can in addition also be applied to cultured cells that are being contacted or that have been contacted with the foreign DNA.

DETAILED DESCRIPTION OF THE INVENTION

The present invention is based on the observations that poly-(ADP-ribose) polymerase (PARP) is an enzyme that is involved in regulating the general metabolic state of an eucaryotic cell and that inhibition of this enzyme can be used to influence the metabolic state of cells which are targeted for transformation (or which are being transformed) to increase the efficiency and/or quality of transformation.

In mammal, PARP is a monomeric nuclear Zn-finger protein of about 116 kD that is closely associated with nuclear DNA, particularly with actively transcribed euchromatic regions (Shah et al, 1995, Anal.Biochem. 227:1–13). The protein is normally an inactive enzyme but is known to be activated by nicked or otherwise damaged DNA. Active PARP transfers the ADP-ribose moiety of NAD+ to various nuclear proteins to synthesize a polymer of ADP-ribose bound to these proteins which include PARP itself, polymerases, histones, endonuclease etc. The proteins on which such a ADP-ribose polymer is synthesized become biologically inactive (de Murcia et al, 1994, TIBS 19:172–176; Cleaver al, 1991, Mutation Res. 257:1–18).

The biological function of PARP is largely unknown but the enzyme has been implicated in:

enhancement of DNA repair (Satoh et al, 1992, Nature 356:356–358; Satoh et al, 1993, J. Biol. Chem. 268:5480–5487), recombination events: in general inhibition of PARP is observed to inhibit illegitimate recombination and to increase intrachromosomal recombination but it does apparently not affect extrachromosomal recombination (Farzaneh et al, 1988, NAR 16:11319–11326; Waldman and Waldman, 1990, NAR 18:5981–5988; Waldman and Waldman, 1991, NAR 19:5943–5947), regulation of gene expression : inhibition of PARP is observed to decrease gene expression (Girod et al, 1991, Plant Cell, Tissue and Organ Culture 25:1–12);

reducing the amount of available NAD+ (and by consequence its precursor ATP) : this results in a general slowing down of cell metabolism (Lazebnik et al, 1994, 371:346–347; Gaal et al, 1987, TIBS 12:129–130; Cleaver et al, supra)

It is known that PARP can be efficiently inhibited by a number of compounds (Durkacz et al, 1980, Nature 283:593–596; Sims et al, 1982, Biochemistry 21:1813–1821). Examples of such compounds are certain pyridine analogs such as nicotinamide analoques, including niacinamide, picolinamide, and 5-methyl nicotinamide; purine analogs like methyixanthines; thymidine; pyrazinamide analogs and many aromatic amides such as many benzamide analogs including benzamide, 3-methoxybenzamide and 3-aminobenzamide. For the purpose of this invention a PARP inhibitor is generally understood as any specific inhibitor of poly-(ADP-ribose) polymerase which can be taken up by a eucaryotic cell, particularly a plant cell, and which has a inhibition constant (Ki) which is lower than $1 \times 10^{-5}$, particularly lower than $1 \times 10^{-6}$. Generally it is desired that the PARP inhibitor used with this invention be a compound which in human lymphocytes, cultured in medium containing the inhibitor at a concentration of 2 mM, results in a 80–90% inhibition of PARP (Sims et al, supra). Generally it is also preferred that cells cultured in medium containing the PARP inhibitor retain their capacity of DNA repair.

Particularly preferred PARP inhibitors are those listed above and especially niacinamide (nicotinamide), picolinamide, 5-methylnicotinamide, 2-aminobenzamide, pyrazinamide, theobromine and theophylline. Particularly niacinamide is believed to be a useful inhibitor for the purpose of this invention.

Basically the present invention provides a modification of existing procedures for the genetic transformation of eucaryotic cells, particularly plant cells, by including in the medium in which such cells are cultured a PARP inhibitor such as niacinamide, for a defined period of time. In particular the PARP inhibitor is added to the culture medium at least 1 day prior to the moment (the "contacting time") at which the cells are contacted with foreign DNA comprising one or more genes of interest. However, depending on the purpose, the PARP inhibitor may also be added to the culture medium during and/or after the contacting time or even solely after the contacting time.

In one aspect of this invention treatment of cultured cells, tissues or organs with PARP inhibitors may be used to increase the quality of transformation as measured by the copy number of the transgene and by variation in transgene expression (quality and quantity) in the transformed cells and in organisms obtained from the transformed cells.

In many conventional procedures for genetic transformation of eucaryotic cells, particularly plant cells, cultured cells, tissues or organs will be used as starting material and cells in such cultures will be contacted with foreign DNA comprising at least one gene of interest (i.e. the transgene) under conditions that will promote the uptake of the foreign DNA in the cells and the ultimate integration of the foreign DNA into the genome of the cells.

In one embodiment of the invention it is preferred that a PARP inhibitor is added to the culture medium for a period of at least 2–3 days, preferably at least about 3 days, prior to contacting the cells with the foreign DNA. The exact period in which the cultured cells are incubated in PARP inhibitor containing medium is believed not to be critical but should probably not exceed 4 weeks. It appears that 2–14 days, particularly 3–10 days, is an optimal period and best results were obtained with an incubation period of approximately 4 to 5 days prior to the contacting time. Generally it is believed that 4 days is a useful period for the PARP inhibitor to be added to the culture medium prior to the contacting time.

The concentration of the PARP inhibitor in the medium is also believed to have an effect on the inhibition of PARP, which varies depending on the nature of the cells (species, tissue explant, general culture conditions, etc.) However, within certain concentration ranges, the effect is minimal, especially when the cultured cells are not incubated for longer than 14 days. The optimal concentration range of PARP inhibitor in the medium may vary depending on the species from which the tissue, cell or cell culture is derived, but 250 mg/l (about 2 mM) is believed to be a suitable concentration for many purposes (e.g. for use with material derived from wheat). However, when nicotinamide is used in combination with plant material derived from rice, the concentration of nicotinamide should preferably be between 500 mg/l (about 4 mM) and 1000 mg/l (approx. 8 mM). On the other hand, when nicotinamide is used in combination with plant material derived from corn the concentration of nicotinamide should preferably be 100 mg/l. Likewise, a concentration of 100 mg/l is already effective for wheat-derived plant material, but higher concentrations may be used. The optimal concentration will depend on the nature of the specific PARP inhibitor used, particularly on its strength of inhibition (as measured by its Ki and/or by its percentage inhibition of PARP under standard conditions—Sims et al, supra). It was found for instance that the optimal concentration for nicotinamide is approximately 250 mg/l (i.e. about 2 mM) but it is believed that concentrations up to 1000 mg/l (approx. 8 mM) and as low as 150 mg/l (approx. 1.25 mM), even as low as 100mg/l can be used to good effect. Preferably the nicotinamide concentration should be between 200 and 300 mg/l, i.e. between approximately 1.5 mM and 2.5 mM. In similar conditions, the optimal concentration for more potent PARP inhibitors such as 3-methoxybenzamide is about 0.5 mM, but it is believed that concentrations up to 2 mM and as low as 0.1 mM can be used to good effect. Similar concentrations apply to other PARP inhibitors.

If incubation times of longer than 14 days are used it is believed that the PARP inhibitor concentration should be reduced below 2 mM (e.g. between 0.5 mM and 1.5 mM and particularly approximately 0.8 mM).

For other PARP inhibitors optimal concentrations can be easily established by experimentation in accordance with this invention.

During transformation it is not known whether the integration of the DNA into the genome of the cell occurs immediately after uptake of DNA by the cell. It may very well be that the foreign DNA exists as free DNA within the cell for a certain period after the contacting time. Therefore cultured cells may be further incubated in medium containing a PARP inhibitor during and, for a limited period of time after, contacting the cells with the foreign DNA. Again the length of the incubation period is not critical but is preferably 2–10 days, particularly approximately 4 days. It is preferred that the inhibitor concentration of the PARP inhibitor in the culture medium after the contacting time should be below 2 mM, between 0.8 and 1 mM. If the cells that are to be transformed are not obtained from a cell or tissue culture (e.g. when intact tissue of an organism is contacted directly with DNA, as for example described in WO 92109696) the PARP inhibitor may still be applied to the target cells prior to the contacting time but the addition of the PARP inhibitor to the culture of the transformed cells during or after the contacting time is preferred.

As indicated above, PARP inhibitor treatment of cultured cells for at least 2–3 days increases the quality of transformation. Indeed the number of copies of the foreign DNA is expected to be generally lower and variation in expression profile (level—i.e. the quantity—of expression as well as spatial and time distribution—i.e. the quality—of expression in the transgenic organism) of the gene(s) of interest in the foreign DNA, due to position effects, is decreased. However, at least in this aspect of the invention, the efficiency of transformation can be decreased. The efficiency of transformation as used herein can be measured by the number of transformed cells (or transgenic organisms grown from individual transformed cells) that are recovered under standard experimental conditions (i.e. standardized or normalized with respect to amount of cells contacted with foreign DNA, amount of delivered DNA, type and conditions of DNA delivery, genera, culture conditions etc.).

Therefore it is preferred that the invention is used with transformation procedures that already have a high efficiency, such as Agrobacterium mediated transformation of dicots and direct gene transfer in monocots, particularly cereals (e.g. electroporation or particle bombardment of compact embryogenic callus in cereals—see WO 92/09696). Indeed these transformation procedures are generally highly efficient but the quality of transformation is generally poor. Position effects are large and, especially with direct gene transfer, the copy number of the transgene is often exceptionally high making analysis and selection of optimal transformants, as well as further breeding with the transformants, difficult.

In another aspect of this invention treatment of cultured plant cells for a short period of time (i.e. 1 day to maximally 2 days) prior to, or after contacting the cells with DNA may be used to increase the efficiency of Agrobacterium mediated transformation of plant species, such as many monocots, particularly the major cereals such as wheat and corn, for which this method is generally inefficient. It is believed that treatment of cultured plant cells during the contacting time may result in a lower transformation efficiency, and might therefore not be suitable for this aspect of this invention. Likewise, it is believed that for the purpose of this aspect of the invention, the optimal treatment with a PARP inhibitor is 1 day to maximally 2 days prior to the contacting time, or alternatively 1 to maximally 2 days after the contacting time. In this embodiment of the invention the contacting of the plant cells with the DNA should of course be understood as contacting the cells with an appropriate Agrobacterium strain harboring an artificial T-DNA containing the foreign DNA with the gene(s) of interest. In this embodiment of the invention the quality of transformation is expected not to be affected but this is generally deemed to be of lesser importance since Agrobacterium mediated transformation, being a biological process, already results in a generally low copy number of the transgene in the transformed plant cells.

In accordance with this invention the addition of PARP inhibitors, such as niacinamide, to the culture medium of eucaryotic cells, can be used in combination with any known transformation procedure that requires cells, tissues or organs cultured in vitro as starting cells to be contacted with foreign DNA. The process of this invention is thus generally identical to existing conventional transformation methods except for the fact that at some times during the tissue culture of the cells, a PARP inhibitor is added to the culture medium.

The cell of a plant, particularly a plant capable of being infected with Agrobacterium such as most dicotyledonous plants (e.g. Brassica napus) and some monocotyledonous plants, can be transformed using a vector that is a disarmed Ti-plasmid containing the gene(s) of interest and carried by Agrobacterium. This transformation can be carried out using conventional procedures (EP 0,116,718; Deblaere et al, supra; Chang et al, 1994, The Plant Journal 5:551–558). Preferred Ti-plasmid vectors contain the foreign DNA between the border sequences, or at least located to the left of the right border sequence, of the T-DNA of the Ti-plasmid. Of course, other types of vectors can be used to transform the plant cell, using procedures such as direct gene transfer (as described, for example, in EP 0,233,247), pollen mediated transformation (as described, for example, in EP 0,270,356, PCT patent publication "WO" 85/101856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536,475). Cells of monocotyledonous plants such as the major cereals including corn, rice, wheat, barley, and rye, can be transformed (e.g. by electroporation) using wounded or enzyme-degraded intact tissues capable of forming compact embryogenic callus (such as immature embryos in corn), or the embryogenic callus (such as type I callus in corn) obtained thereof, as described in WO 92109696. In case the plant to be transformed is corn, other recently developed methods can also be used such as, for example, the method described for certain lines of corn by Fromm et al., 1990, Bio/Technology 8:833; Gordon-Kamm et al., 1990, Bio/Technology 2:603 and Gould et al., 1991, Plant Physiol. 95:426. In case the plant to be transformed is rice, recently developed methods can also be used such as, for example, the method described for certain lines of rice by Shimamoto et al., 1989, Nature 338:274; Datta et al., 1990, Bio/Technology 8:736; and Hayashimoto et al., 1990, Plant Physiol. 93:857; Hiei et al, 1994, The Plant Journal 6:271–282).

The transformed cell can be regenerated into a mature plant and the resulting transformed plant can be used in a conventional breeding scheme to produce more transformed plants with the same characteristics or to introduce the gene(s) of interest in other varieties of the same related plant species. Seeds obtained from the transformed plants contain the chimeric gene(s) of this invention as a stable genomic insert. Thus the gene(s) of interest when introduced into a particular line of a plant species can always be introduced into any other line by backcrossing.

In animals pluripotent embryonic or somatic stem cells can be used as target for transformation (Capecchi et al, 1989, TIG:5:70–76).

The transformed cells and organisms of any plant or animal species, produced by the process of this invention, contain the foreign DNA as a stable insert in their genome, particularly in regions of the genome that remain transcriptionally active in the untransformed cells that have been exposed to a PARP inhibitor in accordance with this invention. As described above it is believed that in cells treated with a PARP inhibitor for at least 3 days, particularly for at least 4 days, only a limited number of genomic regions will remain transcriptionally active. In this regard the transformed cells, obtained with this process of the invention, will be characterized by having the foreign DNA integrated in a limited number of genomic regions. That the transformed cell or organism was obtained by this process of the invention can thus be easily ascertained by 1) culturing transformed cells or tissues under conditions that are similar as those in which the untransformed cells or tissues were grown or incubated prior to the integration of the foreign DNA in the genome (i.e. incubating in medium containing 250 mg/l niacinamide for 4–5 days prior to the contacting time), and 2) monitoring the expression of at least one transgene in the foreign DNA that is expected to be expressed under normal tissue culture conditions (i.e. a selectable marker gene under the control of a promoter that directs expression in tissue culture). Under the above conditions the transformed cells or tissues of this invention express the relevant transgene in the tissue culture at essentially the same levels whether or not a PARP inhibitor is present in the culture medium. It is thus expected that, for instance after 4–5 days of culturing of the transformed cells in medium containing the PARP inhibitor, mRNA levels are not signicantly decreased, i.e. do not become lower than 75%, preferably not become lower than 90%, when compared to the mRNA levels observed in cells cultured in medium not containing the inhibitor. Indeed, if the relevant transgene is integrated in other regions of the genome (i.e. in regions that are normally not transcriptionally active in cells treated with PARP inhibitor according to this embodiment of the invention), the expression of the relevant transgene is considerably reduced after incubation of the cells in medium containing the PARP inhibitor for at least 3 days, e.g. 4–5 days (i.e. mRNA levels will drop below 75%, particularly below 50%, more particularly below 30%) when compared to the mRNA levels observed in cells cultured in medium not containing the inhibitor).

The method of the present invention can in principle be used to transform eucaryotic cells with any foreign DNA. Generally the foreign DNA comprises at least one gene of interest comprising 1) a promoter region with a promoter capable of directing transcription of DNA into a RNA in cells of the eucaryotic, e.g. plant, species that is to be transformed and 2) a coding region coding for a RNA or protein. Most often the gene of interest will also comprise 3) a 3' untranslated region of a eucaryotic gene containing a polyadenylation signal. The promoter can be selected to direct expression in selected tissues of the eucaryotic organism. Such a tissue-selective promoter is not expected to direct expression in other non-selected tissues. For instance promoters are known that direct expression selectively in stamen tissues of a plant and such promoters have been used to produce male sterile plants and other plants useful for producing hybrids (EP 344029; EP 412911; WO 9213956; WO 9213957; Mariani et al, 1990, Nature 347:737–741; Mariani et al, 1992, Nature 357:384–387).

It is believed that the method of the present invention is particularly useful to transform eucaryotic cells with at least one gene of interest comprising a tissue-selective promoter, such as a stamen selective promoter, especially if expression of the gene of interest in the organism, such as a plant, outside the selected tissues (where the tissue-selective promoter is active, i.e. directs expression) is undesired for example because the gene product (for instance a protein such as a ribonuclease, e.g. bamase) is capable of killing or disabling the cells in which they are produced. In such cases expression of the gene of interest in tissue culture, or in non-selected tissues of the organisms can negatively affect the quality as well as the apparent efficiency of transformation. When the method of this invention is used, the overall efficiency of transformation may be reduced but the average quality of transformation is expected to be significantly improved because of lower copy number of the gene of interest in the genome of the transformed cells and because of reduced position effects i.e. the general integration of the gene of interest in the genomes at locations that minimally affect the transcriptional properties of the promoter of the transgene.

The foreign DNA used in the method of this invention generally also comprises a selectable marker gene the expression of which allows the selection of transformed cells (or organisms) from non-transformed cells (or organisms). Such selectable marker gene generally encodes a protein that confers to the cell resistance to an antibiotic or other chemical compound that is normally toxic for the cells. In plants the selectable marker gene may thus also encode a protein that confers resistance to a herbicide, such as a herbicide comprising a glutamine synthetase inhibitor (e.g. phosphinothricin) as an active ingredient. An example of such genes are genes encoding phosphinothricin acetyl transferase such as the sfr or sfrv genes (EP 242236; EP 242246; De Block et al, 1987 EMBO J 6:2513–2518).

The inventors also found that the initial reaction of cells, particularly cells contacted with PARP inhibitors, is a stress reaction which enhances free radical production by the cell. However, this stress only lasts for a limited period of time after which further contact with the PARP inhibitor causes a decrease in cell metabolism, particularly a decrease in electron flow in the mitochondral electron transport chain. Therefore, the invention also relates to a new method to assess the agronomical fitness of a population of transformed plants to determine in which lines the plants have a foreign DNA integrated in their genomes in a way that agronomical performance is not or substantially not affected.

The assay is based on comparative reaction of transgenic cells and corresponding untransformed controls to stress conditions.

The method comprises exposing the transgenic cells to stress conditions which induce the production of free radicals in the tissues or the cells, measuring the amount of free radicals produced in the transgenic cells with the amount of free radicals produced in control cells exposed to similar stress conditions. Preferably the cells of the transgenic organism to be assayed are exposed to stress conditions by being treated with a substance which induces increasing osmotic and/or salt stress on the cells.

The properties of PARP inhibitors, such as niacinamide, to enhance free radical production in cells incubated with the inhibitor for not longer than 2 days, preferably not longer than 1 day, can be used to assay the (relative) fitness of a population of transgenic eucaryotic organisms, particularly plants.

The term fitness used herein is intended to designate the agronomical performance of a population of plants, as measured for instance by its yield (e.g. its seed yield) as compared to a given reference population. Agronomical performance is generally thought to be correlated with the general resistance of the plants to a range of stress conditions which are likely to be encountered in the field locations where the plants are normally grown. For any population of transformed plants (i.e. a transgenic line) the relevant reference population is a population of untransformed plants of the same variety.

It is known that in transformed plants and other organisms transgene expression may be qualitatively and quantitatively influenced by the genomic domain in which the transgene(s) are integrated, that undesired transgene expression may interfere with cell metabolism (e.g. when the transgene encodes a cytotoxic protein), that mutations may be induced in the transformed organism either by somaclonal variation or by insertional inactivation of endogenous genes by the transgene(s), or that expression of endogenous genes may be deregulated by sequences in the foreign DNA. As a consequence many transformed lines may not be agronomically useful.

The assay of this invention will for example allow to identify a line (i.e. a group of genetically similar plants) of transformed plants that have the transgene(s) integrated in regions that minimally affect the fitness of the plants, thus avoiding the extensive laboratory, greenhouse and/or field evaluations which are normally required to identify the transformants with the best agronomical properties.

The assay in accordance with this invention essentially comprises the incubation of cells or tissues of transformed plants of a particular transgenic line (e.g. callus, hypocotyl explants, shoots, leaf disks, whole leaves etc.) preferably with a PARP inhibitor (although for some plant species this is not necessary) under a range of conditions which induce the production of a different amount of free radicals in the tissues. An incubation time of approximately one day is normally sufficient to generate the desired amount of free radicals. Appropriate controls, i.e. untransformed tissues obtained from untransformed plants at the same developmental stage and grown in the same conditions as the transformed plant from which the transformed tissue was obtained, are subjected to the same treatment. Preferably the untransformed line is identical to the transgenic line except for the presence of the transgene(s).

For each plant line (control or transformant) it is preferred that a number of plants is assayed.

Useful conditions for the incubation of the untransformed and transformed tissues are those which induce increasing osmotic and salt stress in the incubated cells or tissues. For example a series of buffers with different salt concentrations containing a PARP inhibitor can be made. A useful buffer series is a K-phosphate buffer containing 2% sucrose and 250 mg/l niacinamide in which the K-phosphate concentration is increased from anywhere between 10 to 80 mM (e.g. in steps of 5 mM, i.e. 10, 20, 25, 30, 35, 40, 45, 50, 55, 60 mM). The K-phosphate concentrations will induce mild but increasing salt and osmotic stress in plant cells. The niacinamide in the medium further enhances radical production and stress on the plant cells. The range of K-phosphate concentrations used will depend on the natural sensitivity of the plant species (or if desired the plant line) to the salt and osmotic stress. In sensitive plant species, which will not tolerate high salt stress, the maximum K-phosphate concentration may for instance be 50 mM, in less sensitive species this maximum K-phosphate concentration can be increased up to 70 or 80 mM or even higher. For each plant species the minimum and particularly the maximum salt (e.g. K-phosphate) concentration can be determined experimentally for an untransformed line—the only requirement is that at all concentrations used the plant tissue remains viable. Although the addition of a PARP inhibitor to the medium, such as niacinamide, is preferred it is not required for assaying plant species that are very sensitive to salt and/or osmotic stress.

After the one day incubation the capacity of the transformed and control tissues to reduce 2,3,5-triphenyltetrazolium chloride (TTC) is measured e.g. by the following procedure which is modified from Towill and Mazur (su*pra*):

incubate the tissues for 1 to 4 hours in K-phosphate buffer (pH 7.4) containing 10 mM TTC and 0.1% Tween20. As a control similar plant material is incubated in the same buffer withour TrC.

extraction of reduced TTC (e.g. freezing at −70° C. followed by thawing at 40° C. and shaking the plant material in ethanol for 45–60 minutes)

spectrophotometric quantification of reduced TTC at 485 nm (optical density $OD_{485}$; for chlorophyll poor plant material or 545 nm ($OD_{545}$; Or chlorophyll rich plant material). The O.D. of the control extract is subtracted from the OD of the TTC-reacted extracts. In the above conditions 0.1 mM reduced TTC corresponds to an $OD_{485}$ of 0.214 or OD545, of 1.025 (light path 1 cm).

the reducing capacity of the transformed plant line is compared to that of the control line.

The amount of reduced TTC is determined by the intensity of the cytochromal and alternative respiratory pathways and the radical concentration in the tissues which, in turn are determined by the presence of mutations, the expression of genes affecting the metabolic activity of the plant cells, the developmental stage and the reaction of the tissue to external factors, such as stress factors.

The TTC reducing capacity (as for instance measured by the O.D. at 485 nm) for tissues incubated at high salt concentration (TTC-high) is expressed as the percentage of the TTC reducing capacity of the tissues incubated at a low salt concentration (TTC-low); in other words a TTC-ratio value is calculated as follows:

TTC-ratio=TTC/high.100/TTC.low.

The value of TTC-ratio is a measure of the fitness of a plant line as compared to a control line.

The determination of TTC-low and TTC-high will depend on the sensitivity of the plant species to the applied salt stress. Usually TTClow will correspond to a salt concentration between 10 and 25 mM K-phosphate, e.g. at 20 mM while TTC-high will correspond to a salt concentration between 50 and 80 mM K-phosphate. The only requirement is that TTC-high should be significantly lower than TTC-low; preferably TTC-high should be lower than 50% of TTC-low, particularly lower than 30% of TTC-low. For instance for *Brassica napus*, TTC-low and TTC-high can be typically obtained from tissues incubated at respectively 20mM and 60 mM K-phosphate buffer containing 250 mg/l niacinamide. TTC-high and TTC-low, for both the transformed and untransformed line, will usually be an average obtained from several measurements taken on a number of tissue explants from a number of plants of each line. For instance for each line of Brassica napus about 32 leaf discs (diameter 1 cm) from 8 different plants (i.e. about four leaf discs per plant) can be assayed to determine 32 TTC-high and 32 TTC-low values which are averaged to obtain the TTC-high and TTC-low values used for the calculation of TTC-ratio. Other examples of sample sizes which have been used are 35 shoots from *Arabidopsis thaliana*,or 150 hypocotyl explants derived from about 25 seedlings of *Brassica napus*.

Transformed lines with a value of TTC-ratio which does not deviate more than 20%, preferably not more than 10% of the TTC-ratio value of the control line are selected. These lines are likely to have the transgene(s) integrated in regions that minimally affect the fitness of the plants.

It is clear that additional information considering the fitness of the plant material studied can be obtained by comparing the TTC-reducing capacity of the plant material in absence of a PARP-inibitor with the TTC-reducing capacity of the plant material in the presence of a PARP-inibitor for each experimental point of the buffer series mentioned above.

While the TTC-reduction assay is especially suitable for the identification of transgenic plants, where transgenes are integrated in regions that minimally affect the fitness of the plants, this test can also be succesfully applied to discriminate mutant plants, cells or cell lines from the wild-types.

The TTC-reducing assay can further be used in a modified way to determine the quality and the fitness of plant material, for example plant material to be used in transformation experiments (i.e. whether particular plant material, e.g. explants, is suitable as starting material). To this end the TTC-reducing assay can be adapted for example in the following way:

1. A sample of the plant material to be tested for its suitability for transformation, is incubated for one day in plant culture medium or a buffer containing 2% sucrose and a K-phosphate concentration ranging between 10 and 80 mM, typically around 25 mM, to which a suitable amount of a PARP inhibitor, such as niacinamide has been added. For niacinamide, a preferred concentration to be used is 250 mg/L, although concentrations as low as 100 mg/L and as high as 1000 mg/L may be used. A comparable control sample of the same plant material is incubated under similar conditions without PARP inhibitor.
2. After one day of incubation the capacity of the plant material incubated with PARP inhibitor and the control plant material to reduce TTC is measured by the procedure described above.

The TTC reducing capacity (as for instance measured by the O.D. at 485 nm) for plant material incubated with PARP inhibitor (TTC-INH) is compared with the TTC reducing capacity of the control plant material incubated without PARP inhibitor (TTC-CON) and a ratio (E) is calculated as follows:

E=TTC-INH/TTC-CON

The value E is a measure of the quality and fitness of the plant material, for example explants to be transformed. It is believed that those tissues, wherein the E value is larger than or equals 1, are healthy tissues, which are particularly suitable as starting material for transformation.

The modified TTC-procedure thus allows to select those types of (cultured) plant material especially appropriate for use in a transformation procedure, particularly the procedures of this invention that include the use of a PARP inhibitor.

As the quality of plant material will also be affected by the particular culture conditions used prior to transformation (especially cells, tissues or explants derived from plants recalcitrant to transformation)the assay of this invention is further useful to identify suitable culture conditions to obtain suitable starting plant material. Thus it has beeen found by the inventor that, when culturing plant material from corn, it is preferred to include proline, preferably at a concentration of about 8mM, simultaneously with the PARP inhibitor, in the culture medium.

As already mentioned, incubation of cells or tissues in the presence of a PARP inhibitor for longer than 1 to 2 days leads to a general reduction in cell metabolism, particularly a reduction in the electron flow in the mitochondrial electron transport chain (after the initial increase, characteristic of healthy cells or tissues, during the first day). The period of time required to reduce the metabolism to an optimal level (for the purpose of improving the qualitative aspect of transformation) is that period after which a decrease in TTC-reducing capacity between 20% and 50%, preferably between 30% and 40%, particularly about 35%, is achieved for plant material incubated with a PARP inhibitor (e.g. niacinamide) when compared to control plant material incubated without the PARP inhibitor (i.e. the period after which the E value is between 0.5 and 0.8, preferably is between 0.6 and 0.7, particularly is about 0.65). It is clear that the assays of this invention can be readily adapted by one skilled in the art of the field, for example to suit the needs of the particular cell type, tissue or explant or of the particular species from which the cells, tissues or explants are derived. Furthermore the assay can be adapted to assay a peculiar aspect of fitness of cells, tissue, explant or organism. For instance, it is possible to apply a type of stress different from osmotic or salt stress, such as stress brought about by extreme temperatures, by sublethal treatment with chemicals (e.g. herbicides, heavy metals) or by irradiation with UV. Furthermore, other types of PARP inhibitors, as mentioned before may be used, within the indicated concentration ranges. Although it is believed that for the purpose of the assays defined here, TTC is the most suited substrate, other indicator molecules ,such as MTT (3-(4,5-dimethylthiazol-2-yl)-2,5 diphenyl-2H-tetrazolium) can be used to measure the electron flow in the mitochondrial electron transport chain downstream of the "ubiquinone pool".

Unless otherwise indicated all experimental procedures for manipulating recombinant DNA were carried out by the standardized procedures described in Sambrook et al., 1989, "Molecular Cloning: a Laboratory Manual", Cold Spring Harbor Laboratory, and Ausubel et al, 1994, "Current Protocols in Molecular Biology", John Wiley & Sons.

The polymerase chain reactions ("PCR") were used to clone and/or amplify DNA fragments. PCR with overlap extension was used in order to construct chimeric genes (Horton et al, 1989, Gene 77:61–68; Ho et al, 1989, Gene 20 77:51–59).

All PCR reactions were performed under conventional conditions using the Vent™ polymerase (Cat. No. 254L—

Biolabs New England, Beverley, Mass. 01915, U.S.A.) isolated from Thermococcus litoralis (Neuner et al., 1990, Arch.Microbiol. 153:205–207). Oligonucleotides were designed according to known rules as outlined for example by Kramer and Fritz (1968, Methods in Enzymology 154:350), and synthesized by the phosphoramidite method (Beaucage and Caruthers, 1981, Tetrahedron Letters 22:1859) on an applied Biosystems 380A DNA synthesizer (Applied Biosystems B. V., Maarssen, Netherlands). In the examples MS medium means Murashige and Skoog medium (Murashige and Skoog, 1962, Physiol. Plant 15:473–479).

In the following examples, reference will be made to the following sequence listing and figures:

Seauence Listing

SEQ ID NO 1: T-DNA of plasmid pTHW107

SEQ ID NO 2: plasmid pTS172

SEQ ID NO 3: PT72 promoter contained in plasmid pTS772

SEQ ID No 4: plasmid pVE136

SEQ ID No 5: T-DNA of plasmid pTHW142 Examples

EXAMPLE 1

Tissue Culture of Wheat Embryogenic Callus and *Brassica Napus* Hypocotyl Explants in Media Containing a PARP Inhibitor Wheat embryogenic callus was cultured on W2 medium (see Example 2). When niacinamide was added as PARP-inhibitor to the medium at a concentration of 250 mg/l (approx. 2 mM) it was observed that after 4 days the growth of the tissue was slowed down considerably (to approximately 30% of the normal rate after 4 weeks) but the tissue remained viable for extended periods of time (i.e. at least one month). If niacinamide was subsequently removed from the medium the tissue started to grow normally again. It was also observed that after 4–5 days of incubation of the plant tissue with niacinamide, the TTC-reducing capacity (Towill and Mazur, 1975, Can J. Bot. 53:1097–1102) of the tissue was substantially decreased probably indicating a reduction of the production of free radicals and decreased mitochondrial electron transport.

Similar observations were made when Brassica napus hypocotyl explants were cultured on A5 medium (see Example 3) containing 250 mg/l niacinamide. It was also observed that, in Brassica napus tissue cultured on medium containing niacinamide, no anthocyanin was produced; normally anthocyanin in tissue culture is produced in stress conditions. In addition it was observed that after 4–5 days of incubation of the plant tissue with niacinamide, the concentrations of hydroxyl free radical and dehydroascorbate in the explants were drastically decreased.

It was also observed that, after a 4 day incubation in niacinamide containing medium, the percentage of cultured cells that were in G2 phase of the cell cycle was considerably increased (up to 45% of all cells in the culture). The above observations are interpreted as indicating that treating cultured cells with a PARP inhibitor for about 4–5 days generally results in:

1) a significant reduction of the response of the cultured cells to stress as measured for instance by free radical and/or anthocyanin production , and 2) a reduction of the general metabolism of the cultured cells to a very basic level as indicated by the fact that the tissue growth was slowed down, and the TTC reducing capacity was decreased while the tissue remained viable.

It is inferred that under these conditions many genes in cells (e.g. cultured cells) that would normally be switched on in response to stress (such as during transformation conditions) will in fact no longer be induced. It is expected that in such cells which only display a very basic metabolism, mainly general "housekeeping genes", i.e. genes that are expressed in any cell irrespective of its differentiated state or metabolic or physiological condition, are expressed. As it is believed that foreign DNA is preferably inserted in portions of the genome that are transcriptionally active it follows that treatment with PARP inhibitors will condition eucaryotic cells to incorporate any foreign DNA preferentially in genomic regions which are transcribed in all cells and not in regions of the genome which would only be transcribed under certain conditions, i.e. stress conditions, or during differentiation. This means that the number of locations in which foreign DNA will be integrated, and the concomitant variation in expression profile of the transgene(s), will be reduced. It is further believed that this will enhance integration of foreign genes of interest in such locations which in turn will result in a more reliable and faithful expression of these genes which will be less affected by cell differentiation or cell physiological and biochemical changes due to for instance environmental conditions.

EXAMPLE 2

Transformation of Wheat With a Bamase Gene Under the Control of a Stamen-specific Promoter using the Particle Bombardment The Wheat Spring variety Pavon is grown in a greenhouse or conditioned room at 23–24° C. during daytime and 1820° C. at night, with a photoperiod of 16 hours light and 8 hours dark. Developing seeds (white-greenish with white semi-liquid endosperm) were harvested, sterilized by incubation for 1 minute in 70% ethanol followed by 15 minute incubation in 1.3% NaOCl+0.1% Tween 20, and washed with sterile water. The sterilized seeds were either used directly or were stored for one day at 4–7° C.

Immature embryos of about 1 mm in size were isolated and were placed, with the scutellum upwards, on callus inducing medium W1 (MS medium supplemented with 3% sucrose, 40 mg/l adenine.$SO_4$, 0.5 mg/l thiamine.HCl, 0.5 g/l 2-[N-Morpholino] ethane sulfonic acid (Mes) pH 5.8, 0.5% agarose, 0.5 to 2.5 mg/l $CuSO_4.5H_2O$, 25 mg/l acetylsalicylic acid and 2 mg/l 2,4-dichlorophenoxyacetic acid (2,4-D)) and were incubated for 3 weeks at 27° C. in the dark.

Embryogenic sections of the developing callus were isolated, placed on callus maintenance medium W2 (W1 medium but without acetylsalicylic acid and with only 0.5 mg/l $CuSO_4.5H_2O$ and 1 mg/l 2,4-D), and incubated for 3 weeks at 24–25° C. in the light (approx. 20 mEinsteinsis/$m^2$ (with a photoperiod of 16 hours light and 8 hours dark).

About 2 weeks prior to bombardment the calli were cleaned up by removal of non-morphogenic (i.e. the non-embryogenic and nonmeristematic) parts and were subcultured on W2 medium.

For bombardment the calli were divided into small pieces with an average maximum diameter of about 2–3 mm. These pieces were placed at the center of a 9 cm Petridish containing W2 medium in a circle with a diameter of approx. 0.5 cm. When required niacinamide (250 mg/l) was added to the W2 medium and the tissue pieces were maintained under these conditions for 4 days after they were bombarded.

Bombardment was carried out using the Biolistic PDS-1000/He apparatus (Bio-Rad). Preparation of the microcarriers (0.4–1.2m) and the coating of the microcarriers with DNA was essentially carried out according to the manufacturer's instructions. The Petridishes containing the calli were placed at level 2 of the apparatus and the bombardment was done at 1550 psi.

For the transformation experiments the following plasmid DNA was used.

plasmid DVE136, the sequence of which is given in SEQ ID No 4. This plasmid contains the following chimeric genes:

P35S-bar-3'nos

PCA55-bamase-3'nos in which P35S is the 35S promoter of the Cauliflower Mosaic virus, bar is a DNA encoding phosphinothricin acetyltransferase (EP 242236), 3'nos is the 3' untranslated end of the Agrobacterium T-DNA nopaline synthase gene, PCA55 is a stamen-specific promoter from corn gene CA55 (WO 9213957), and bamase is a DNA encoding bamase (Hartley, 1988, J. Mol. Biol.202:913–915)

plasmid PTS172 the sequence of which is given in SEQ ID No 2. This plasmid contains the following chimeric genes:

P35S-bar-3'g7

PE1-bamase-3'nos in which in which P35S is the 35S promoter of the Cauliflower Mosaic virus, bar is a DNA encoding phosphinothricin acetyltransferase (EP 242236), 3'g7 is the 3' untranslated end of the Agrobacterium T-DNA gene 7, PE1 is a stamen-specific promoter from rice gene E1 (WO 9213956), bamase is a DNA encoding bamase (Hartley, 1988, J. Mol. Biol.202:913–915), and 3'nos is the 3' untranslated end of the Agrobacterium T-DNA nopaline synthase gene, plasmid DTS772 which is identical to pTS172 except that the region between nucleotides 2625–4313 of pTS172, containing PE1, is replaced by the sequence of SEQ ID No 3 containing the PT72 promoter. Thus, plasmid pTS772 contains the following chimeric genes:

P35S-bar-3'g7

PT72-bamase-3'nos in which PT72 is a stamen-specific promoter from rice gene 172 (WO 9213956)

The bombarded calli were transferred to selective medium W2 containing 2.5 mg/l phosphinothricin (PPT) and, if neccesary, 100 mg/l niacinamide. The calli that were placed on medium containing niacinamide were transferred after 4 days to niacinamide-free W2 medium containing 2.5 mg/l PPT. The cells were cultured at 24–25° C.

After two weeks the calli were subcultivated on W2 medium and after a further two weeks the growing parts of the calli were transferred to regeneration medium W4 (W1 medium but without acetylsalicylic acid and with only 0.5 mg/l CuSO$_4$.5H$_2$O and 0.5 mg/l 2,4D). Calli were subcultivated every two weeks at which time the nonmorphogenic parts of the calli were removed. When the calli started to form shoots they were transferred to W5 medium (W1 medium with half concentrated MS medium and only 0.5 mg/l CuSO$_4$.5H$_2$O and without acetylsalicylic acid and 2,4D, but supplemented with 50 mg/l myo-inositol, 0.25 mg/l pyridoxine.HCl and 0.25 mg/l nicotinic acid) containing 2.5 mg/l PPT. For the rest of the procedure temperature was maintained at a maximum of 24° C. The calli were subcultivated every 34 weeks. Once the shoots started to elongate and small roots started to form, the whole calli (or if possible individual shoots) were transferred to 1 liter vessels with W6 medium (half-concentrated MS medium supplemented with 1.5% sucrose, 50 mg/l myo-inositol, 0.25 mg/l pyridoxine.HCl, 0.25 mg/lnicotinic acid, 0.5 mg/l thiamine.HCl, 0.7% agar (Difco) pH 5.8 and 0.5 mg/l CuSO$_4$.5H$_2$O) containing 2.5 mg/l PPT. Once the shoots and roots had grown out, individual shoots were separated from each other and transferred to 1 l vessels containing W6 medium with 2.5 mg/l PPT. Well developed shoots are tested for PPT resistance by means of the TLC assay (De Block et al, 1987, EMBO 6:251-32518) or by direct assay of ammonium production in the tissue (see e.g. De Block et al, 1995, Planta 197: 619–626). Transformed shoots were finally transferred to the greenhouse into soil.

For analysis of the results the transformed plants could be subdivided according to the niacinamide treatment of the parent calli during tissue culture. Thus the following groups were distinguished:

| Group | Niacinamide treatment |
|---|---|
| None | No treatment |
| Before 100 | 100 mg/l niacinamide for four days prior to bombardment |
| Before 250 | 250 mg/l niacinamide for four days prior to bombardment |
| Before/After | 250 mg/l niacinamide for four days prior to bombardment plus 100 mg/l niacinamide for four days after bombardment |

Results of the experiments are presented in Tables 1, 2 and 3. Plants could be obtained only from bombarded calli that were treated with niacinamide. For the plants that were transformed with plasmid pTS172 it was demonstrated that the foreign DNA, comprising the chimeric PE1-bamase-3'nos and P35S-bar-3'g7, was stably incorporated in the wheat genome in 2 to 3 copies on the average. The fact that variation in expression profile (e.g. tissue-specificity) of the transgenes, especially the chimeric bamase genes, was decreased in transformed cells was evident from the fact that male-sterile plants that otherwise looked completely healthy could be obtained only from bombarded calli treated with niacinamide. It is believed that this is due to a more faithful expression characteristics (i.e. lack of expression) of the integrated stamen-selective bamase gene in these calli and shoots regenerated from these calli. In the control calli undesired expression of the bamase gene in tissue cultured cells might have prevented recovery of any transformed plants from these calli. It is expected that to obtain the same number of male-sterile wheat plants from control calli a much larger number of calli would have to be bombarded.

TABLE 1

Results of wheat transformation experiments Plasmid pTSI72

| Treatment | Nr of bombarded calli | Nr of PPT-resistant calli recovered | Nr of PPT resistant plants recovered | Nr of MS plants recovered |
|---|---|---|---|---|
| None | 60 | 30 | 1[a] | 0 |
| Before 250 | 125 | 30 | 3 | 3[b] |

[a]This plant proved to be fertile and to be transformed only with the chimeric bar gene
[b]The obtained plants looked healthy and tillered vigorously

TABLE 2

Plasmid PTSTT2

| Treatment | Nr of bombarded calli | Nr of PPT-resistant calli recovered | Nr of PPT resistant plants recovered | Nr of MS plants recovered |
|---|---|---|---|---|
| None | 250 | 22 | 0 | 0 |
| Before | 250 | 210 | 75 | 7 | 3[a)b)] |
| Before/After | 210 | 45 | 6 | 3[a] |

[a)] The obtained plants looked healthy and tillered vigorously
[b)] Only six plants could be analyzed for MS phenotype since one of the plants died prematurely.

TABLE 3

Plasmid pVEI36

| Treatment | Nr of bombarded calli | Nr of PPT resistant plants recovered | Nr of MS plants recovered |
|---|---|---|---|
| None | 200 | 1 | 0 |
| Before | 100 | 800 | 8[a)] | 8 |

[a)] The obtained plants looked healthy and tillered vigorously

EXAMPLE 3

Transformation of Oilseed Rare With a Barnase Gene Under the Control of a Stamen-specific Promoter Using Agrobacterium Mediated Transformation.

Hypocotyl explants of Brassica napus were obtained, cultured and transformed essentially as described by De Block et al, 1989, Plant Physiol. 914:694–701 except for the following modifications:

hypocotyl explants were precultured for 3 days on A2 medium (MS, 0.5 g/l Mes (pH 5.7), 1.2% glucose, 0.5% agarose, 1 mg/l 2,4-D, 0.25 mg/l naphthalene acetic acid (NM), 1 mg/l 6-benzylaminopurine (BAP)), and then transferred to the A2 medium with or without niacinamide for another 4 days.

infection medium A3 was MS, 0.5 g/l Mes (pH 5.7), 1.2% glucose, 0.1 mg/l NAA, 0.75 mg/l BAP, 0.01 mg/l giberellinic acid (GA3)

selection medium A5 was 0.5 g/l Mes (pH 5.7), 1.2% glucose, 40 mg/l adenine.$SO_4$, 0.5 g/l polyvinylpolypyrrolidone (PVP), 0.5% agarose, 0.1 mg/l NAA, 0.75 mg/l BAP, 0.01 mg/l GA3, 250 mg/l carbenicillin, 250 mg/l triacillin, 5 mg/l $AgNO_3$.

regeneration medium A6 was MS, 0.5 g/l Mes (pH 5.7), 2% sucrose, 40 mg/l adenine.$SO_4$, 0.5 g/l PVP, 0.5% agarose, 0.0025 mg/l BAP, 250 mg/l triacillin.

healthy shoots were transferred to 1 liter vessels containing rooting medium which was either A8 or A9; A8 consists of 100–130 ml half concentrated MS, 1% sucrose (pH 5.0), 1 mg/l isobutyric acid (IBA), 100 mg/l triacillin added to 300 ml perlite (final pH 6.2); A9 consists of half concentrated MS, 1.5% sucrose (pH 5.8) solidified with agar (0.6%) Hypocotyl explants (with or without niacinamide treatment) were infected with Agrobacterium tumefaciens strain C58C1Rif carrying T-DNA vector pTHW107 and a helper Ti-plasmid pMP90 (Koncz and Schell, 1986, Mol.Gen.Genet. 204:383–396)(or a derivative thereof).

Plasmid pTHW107 is a vector carrying a T-DNA comprising the following chimeric genes:
PTA29-barnase-3'g7
PSSU-bar-3'nos in which PTA29 is the promoter of the TA29 gene of tobacco (EP 344029) and PSSU is the promoter of the gene of Arabidoosis thaliana encoding the small subunit of Rubisco. The complete sequence of the T-DNA of pTHW107 is presented in SEQ ID No 1.

Where required niacinamide (250 mg/l) was added to the media for the last 4 days prior to infection with Agrobacterium. Plants regenerated from transformed calli obtained on niacinamide cultured cells were observed to have a low copy number as well as to display less variation in the expression profile of the transgenes (results summarized in Table 4). Five plants regenerated from the calli obtained by transformation including niacinamide and five plants regenerated from the calli obtained by conventional transformation without niacinamide inclusion, were analyzed by Southern hybridization to determine the copy number of the transgenes, and were further analyzed for reproductive phenotype. In the non-treated group, a substantial number of regenerated plants proved not to have a transgene integrated in their nuclear DNA.

TABLE 4

| Treatment | Id. No. | Vegetative phenotype[a] | Reproductive phenotype[b] | Copy No. of the transgenes[c] | Phenotype of the F1-progeny[d] |
|---|---|---|---|---|---|
| no treatment | 1 | stressed | sterile | 3 | stressed/sterile |
| | 2 | stressed | sterile | 4–6 | ND |
| | 3 | stressed | sterile | 3 | stressed/sterile |
| | 4 | normal | sterile | 1 | normal/sterile |
| | 5 | stressed | (bud fail) | ND | ND |
| Before 250 | 1 | normal | sterile | 1 | normal/sterile |
| | 2 | normal | sterile | 3 | normal/sterile |
| | 3 | normal | sterile | 1 | ND |
| | 4 | normal | sterile | 3 | ND |
| | 5 | normal | sterile | 2 | ND | a. Vegetatively stressed plants have a small size and flower early, leaves are oblong and dark green.
b. Reproductive phenotype regards male sterility; in flowers where the buds fell off prematurely this phenotype was not scored, except where some buds resulted in flowers.
c. Copy number of the transgenes was estimated by comparative Southern. ND: not determined.
d. FI-progeny was obtained by pollinating the transforrned plants with pollen obtained from an untransformed N90-740 line. FI-Progeny resistant to phosphinotricin was scored for vegetative and reproductive phenotype.

EXAMPLE 4

Agrobacterium-mediated Transformation of Oilseed Rare Using Niacinamide in the Culture Medium.

Hypocotyl explants of Brassica napus were obtained as described in Example 3. Four groups of 200 hypocotyl explants each, were either not treated with niacinamide (indicated in table 4 as NONE), treated with 250 mg/l niacinamide for 1 day prior to infection with Agrobacterium (BEFORE), treated for 2 days during the infection with 250 mg/l niacinamide (DURING), or treated for 1 day after the Agrobacterium infection with 250 mg/l niacinamide (AFTER). All hypocotyl explants were infected with Agrobacterium tumefaciens strain C58C1Rif carrying T-DNA vector pTHW142 and a helper Ti-plasmid pMP90 (Koncz and Shell, 1986 supra)(or a derivative thereof).

Plasmid pTHW142 is a vector carrying a T-DNA comprising the following chimeric genes:

PSSU-bar-3'g7 p35S-uidA-3'35S

In which uidA is a DNA encoding b-glucuronidase (Jefferson et al., 1986, Proc. Natl. Acad. Sci. USA 83, 8447–8451) and 3' 35S is the 3' untranslated end of the cauliflower mosaic virus 35S transcript.

The complete sequence of the T-DNA of pTHW142 is presented in SEQ ID No 5.

After the Agrobacterium infection, hypocotyl explants were transferred to selection medium A5, and if appropriate to A5 medium containing 250 mg/l niacinamide. The hypocotyl explants that were placed on medium containing niacinamide were transferred after 1 day to niacinamide-free selection medium A5. After 5 weeks on selective medium the number of transformed calli was scored. b-glucuronidase expression was verified in the obtained calli using established protocols (Jefferson et al.,1986). The results are summarized in Table 5. Niacinamide treatment either before or after the Agrobacterium infection significantly increase the transformation efficiency.

TABLE 5

| Treatment | Transformation frequency[a] | Remarks[b] |
|---|---|---|
| NONE | 16% | small, green calli |
| BEFORE | 32% | large, green calli |
| DURING | 16% | very small, light green calli large, green calli |
| AFTER | 29% | developing shoots |

[a]. Determined as the number of transformed calli (PPT-resitant and GUS-positive) developing per 100 hypocotyl explants
[b]. Size determination was as follows:
very small: callus diameter of approximately 1–2 mm
small: callus diameter of approximately 2–3 mm
large: callus diameter of approximately 5 mm All publications cited in this application are hereby incorporated by reference.

What is claimed:

1. A process for producing transgenic plant cells, said process comprising the steps of:
   a) contacting a culture of plant cells with an inhibitor of poly (ADP-ribose) polymerese, prior to transformation, for a period of time sufficient to reduce the response of the cultured plant cells to stress and to reduce the metabolism of said cultured plant cells;
   b) contacting said cultured plant cells with a foreign DNA comprising at least one gene of interest under conditions wherein said foreign DNA is taken up by said plant cells and said gene of interest is stably integrated in the nuclear genome of said plant cells; and
   c) recovering said transgenic plant cells from said culture.

2. The process of claim 1, wherein said inhibitor of poly (ADP-ribose) polymerase is selected from the group consisting of niacinamide, picolinamide, 5-methyl nicotinamide, methylxanthines, thymidine, benzamide, 3-methoxybenzamide, 3-aminobenzamide, 2-aminobenzamide, pyrazinamide, theobromine and theophylline.

3. The process of claim 2, wherein said inhibitor is niacinamide.

4. The process of claim 3, wherein said inhibitor is present at a concentration of about 150 mg/l to about 1,000 mg/l.

5. The process of claim 3, wherein said inhibitor is present at a concentration of about 200 m/gl to about 500 mg/l.

6. The process of claim 3, wherein said inhibitor is present at a concentration of about 250 mg/l.

7. The process of claim 1, wherein said cultured plant cells are contacted with said inhibitor of poly (ADP-ribose) polymerase for about 2 to about 28 days, prior to contacting with said foreign DNA.

8. The process of claim 1, wherein said cultured plant cells are contacted with said inhibitor of poly (ADP-ribose) polymerase for about 3 to about 14 days, prior to contacting with said foreign DNA.

9. The process of claim 1, wherein said cultured plant cells are contacted with said inhibitor of poly (ADP-ribose) polymerase for about 4 days, prior to contacting with said foreign DNA.

10. The process of claim 1, further comprising before step c) culturing said plant cells in a medium containing said inhibitor of poly (ADP-ribose) polymerase for approximately 1 to 4 days.

11. The process of claim 10, wherein said plant cells are further cultured in a medium containing said inhibitor of poly (ADP-ribose) polymerase for a proximately 2 to 4 days.

12. A process for increasing the frequency of obtaining transgenic plant cells via Agrobacterium-mediated transformation, said process comprising the steps of:
   a) contacting plant cells with a foreign DNA comprising at least one gene of interest, under conditions wherein said foreign DNA is taken up by said plant cells and said gene of interest is stably integrated in the nuclear genome of said cells to produce transgenic plant cells;
   b) contacting said transgenic plant cells with an inhibitor of poly (ADP-ribose) polymerase; and
   c) further culturing said transgenic plant cells in a medium containing said inhibitor of poly (ADP-ribose) polymerase for a period of time of approximately 1 to 14 days.

13. A process for increasing the frequency of obtaining transgenic plant cells via Agrobacterium-mediated transformation, said process comprising the steps of:
   a) contacting plant cells with a foreign DNA comprising at least one gene of interest, under conditions wherein said foreign DNA is taken up by said plant cells and said gene of interest is stably integrated in the nuclear genome of said cells to produce transgenic plant cells;
   b) contacting said transgenic plant cells with an inhibitor of poly (ADP-ribose) polymerase; and
   c) further culturing said transgenic plant cells in a medium containing said inhibitor of poly (ADP-ribose) polymerase for a period of time of approximately 1 to 4 days.

14. The process of claim 12, wherein said inhibitor of poly (ADP-ribose) polymerase is selected from the group consisting of niacinamide, picolinamide, 5-methyl nicotinamide, methylxanthines, thymidine, benzamide, 3-methoxybenzamide, 3-aminobenzamide, 2-aminobenzamide, pyrazinamide, theobromine and theophylline.

15. A process for increasing the frequency of obtaining transgenic plant cells via Agrobacterium-mediated transformation, said process comprising the steps of:
   a) contacting a culture of plant cells with an inhibitor of poly (ADP-ribose) polymerase, prior to transformation, for a period of approximately 1 to 2 days; and
   b) contacting said plant cells with an Agrobaderium comprising a T-DNA comprising at least one gene of interest under conditions wherein said T-DNA is taken up by said plant cells and said gene of interest is stably integrated in the nuclear genome of said plant cells to produce said transgenic plants cells.

16. The process of claim 15, wherein said transgenic plant cells are further cultured in said medium containing said inhibitor of poly (ADP-ribose) polymerase for approximately 1 to 2 days.

17. The process of claim 15, wherein said inhibitor of poly (ADP-ribose) polymerase is selected from the group consisting of niacinamide, picolinamide, 5-methyl nicotinamide, methylxanthines, thymidine, benzamide, 3-methoxybenzamide, 3-aminobenzamide, 2-aminobenzamide, pyrazinamide, theobromine and theophylline.

18. The process of any one of claims 1, or 15 wherein said gene of interest comprises a promoter which directs expression selectively in certain cells of tissues of a plant.

19. The process of claim 18, wherein said gene of interest comprises a promoter which directs expression selectively in stamen cells.

20. The process of claim 19, wherein said gene of interest comprises a promoter which directs expression selectively in anther cells.

21. The process of claim 18, wherein said gene of interest encodes a protein, which, when produced in said plant cells, kills or disables said plant cells.

22. The process of claim 21, wherein said gene of interest encodes a ribonuclease.

23. The process of claim 22, wherein said ribonuclease is a barnase.

24. The process of any one of claims 1 or 15, wherein a transgenic plant having said foreign DNA with said gene of interest stably integrated in its genome is regenerated from said transgenic plant cells.

25. The process of claim 24, wherein said transgenic plant is a monocotyledonous plant.

26. The process of claim 25, wherein said monocotyledonous plant is a cereal plant.

27. The process of claim 26, wherein said cereal plant is wheat.

28. The process of claim 12 or claim 13, wherein said gene of interest comprises a promoter which directs expression selectively in certain cells of tissues of a plant.

29. The process of claim 28, wherein said gene of interest comprises a promoter which directs expression selectively in stamen cells.

30. The process of claim 29, wherein said gene of interest comprises a promoter which directs expression selectively in anther cells.

31. The process of claim 28, wherein said gene of interest encodes a protein, which, when produced in said plant cells, kills or disables said plant cells.

32. The process of claim 31, wherein said gene of interest encodes a ribonuclease.

33. The process of claim 32, wherein said ribonuclease is a barnase.

34. The process of claim 12 or claim 13, wherein a transgenic plant having said foreign DNA with said gene of interest stably integrated in its genome is regenerated from said transgenic plant cells.

35. The process of claim 34, wherein said transgenic plant is a Brassica plant.

* * * * *

SEQUENCE LISTING

```
<160> NUMBER OF SEQ ID NOS: 5

<210> SEQ ID NO 1
<211> LENGTH: 4946
<212> TYPE: DNA
<213> ORGANISM: Artificial Sequence
<220> FEATURE:
<223> OTHER INFORMATION: Description of Artificial Sequence: T-DNA of
      plasmid pTHW107
<220> FEATURE:
<221> NAME/KEY: misc_feature
<222> LOCATION: Complement((1)..(25))
<223> OTHER INFORMATION: T-DNA right border (RB)
<220> FEATURE:
<221> NAME/KEY: misc_feature
<222> LOCATION: Complement((97)..(330))
<223> OTHER INFORMATION: 3'g7: 3' untranslated region containing the
      polyadenylation signal of gene 7 of Agrobacterium
      T-DNA
<220> FEATURE:
<221> NAME/KEY: misc_feature
<222> LOCATION: Complement((331)..(882))
<223> OTHER INFORMATION: bar: region coding for phosphinotricin acetyl
      transferase
<220> FEATURE:
<221> NAME/KEY: misc_feature
<222> LOCATION: Complement((883)..(2608))
<223> OTHER INFORMATION: promoter region of Rubisco small subunit gene
      of Arabidopsis thaliana (PSSU)
<220> FEATURE:
<221> NAME/KEY: misc_feature
<222> LOCATION: Complement((2658)..(3031))
<223> OTHER INFORMATION: 3' nos: 3' untranslated region containing the
      polyadenylation signal of the nopaline synthase
      gene of Agrobacterium T-DNA
<220> FEATURE:
<221> NAME/KEY: misc_feature
<222> LOCATION: Complement((3032)..(3367))
<223> OTHER INFORMATION: barnase: region coding for barnase
<220> FEATURE:
<221> NAME/KEY: misc_feature
<222> LOCATION: Complement((3368)..(4876))
<223> OTHER INFORMATION: PTA29: promoter region of TA29 gene of
      Nicotiana tabacum
<220> FEATURE:
<221> NAME/KEY: misc_feature
<222> LOCATION: Complement((4922)..(4946))
<223> OTHER INFORMATION: LB: T-DNA left border
```

```
<400> SEQUENCE: 1
aattacaacg gtatatatcc tgccagtact cggccgtcga actcggccgt cgagtacatg      60
gtcgataaga aaaggcaatt tgtagatgtt aattcccatc ttgaaagaaa tatagtttaa     120
atatttattg ataaaataac aagtcaggta ttatagtcca agcaaaaaca taaatttatt     180
gatgcaagtt taaattcaga aatatttcaa taactgatta tatcagctgg tacattgccg     240
tagatgaaag actgagtgcg atattatgtg taatacataa attgatgata tagctagctt     300
agctcatcgg gggatcctag acgcgtgaga tcagatctcg gtgacgggca ggaccggacg     360
gggcggtacc ggcaggctga agtccagctg ccagaaaccc acgtcatgcc agttcccgtg     420
cttgaagccg gccgcccgca gcatgccgcg gggggcatat ccgagcgcct cgtgcatgcg     480
cacgctcggg tcgttgggca gcccgatgac agcgaccacg ctcttgaagc cctgtgcctc     540
cagggacttc agcaggtggg tgtagagcgt ggagcccagt cccgtccgct ggtggcgggg     600
ggagacgtac acggtcgact cggccgtcca gtcgtaggcg ttgcgtgcct tccagggggcc     660
cgcgtaggcg atgccggcga cctcgccgtc cacctcggcg acgagccagg gatagcgctc     720
ccgcagacgg acgaggtcgt ccgtccactc ctgcggttcc tgcggctcgg tacggaagtt     780
gaccgtgctt gtctcgatgt agtggttgac gatggtgcag accgccggca tgtccgcctc     840
ggtggcacgg cggatgtcgg ccgggcgtcg ttctgggtcc attgttcttc tttactcttt     900
gtgtgactga ggtttggtct agtgctttgt tcatctatat ataatgataa caacaatgag     960
aacaagcttt ggagtgatcg gagggtctag gatacatgag attcaagtgg actaggatct    1020
acaccgttgg attttgagtg tggatatgtg tgaggttaat tttacttggt aacggccaca    1080
aaggcctaag gagaggtgtt gagacccta tcggcttgaa ccgctggaat aatgccacgt    1140
ggaagataat tccatgaatc ttatcgttat ctatgagtga aattgtgtga tggtggagtg    1200
gtgcttgctc attttacttg cctggtggac ttggcccttt ccttatgggg aatttatatt    1260
ttacttacta tagagctttc atacctttt tttaccttgg atttagttaa tatataatgg    1320
tatgattcat gaataaaaat gggaaatttt tgaatttgta ctgctaaatg cataagatta    1380
ggtgaaactg tggaatatat atttttttca tttaaaagca aaatttgcct tttactagaa    1440
ttataaatat agaaaaatat ataacattca aataaaaatg aaaataagaa cttcaaaaa    1500
acagaactat gtttaatgtg taaagattag tcgcacatca agtcatctgt tacaatatgt    1560
tacaacaagt cataagccca acaaagttag cacgtctaaa taaactaaag agtccacgaa    1620
aatattacaa atcataagcc caacaaagtt attgatcaaa aaaaaaaaac gcccaacaaa    1680
gctaaacaaa gtccaaaaaa aacttctcaa gtctccatct tcctttatga acattgaaaa    1740
ctatacacaa aacaagtcag ataaatctct ttctgggcct gtcttcccaa cctcctacat    1800
cacttcccta tcggattgaa tgttttactt gtaccttttc cgttgcaatg atattgatag    1860
tatgtttgtg aaaactaata gggttaacaa tcgaagtcat ggaatatgga tttggtccaa    1920
gattttccga gagctttcta gtagaaagcc catcaccaga aatttactag taaaataaat    1980
caccaattag gtttcttatt atgtgccaaa ttcaatataa ttatagagga tatttcaaat    2040
gaaaacgtat gaatgttatt agtaaatggt caggtaagac attaaaaaaa tcctacgtca    2100
gatattcaac tttaaaaatt cgatcagtgt ggaattgtac aaaaatttgg gatctactat    2160
atatatataa tgcttacaa cacttggatt ttttttgga ggctggaatt tttaatctac    2220
atatttgttt tggccatgca ccaactcatt gtttagtgta atactttgat tttgtcaaat    2280
atatgtgttc gtgtatattt gtataagaat ttcctttgacc atatacacac acacatatat    2340
```

-continued

```
atatatatat atatattata tatcatgcac ttttaattga aaaaataata tatatatata    2400
tagtgcattt tttctaacaa ccatatatgt tgcgattgat ctgcaaaaat actgctagag    2460
taatgaaaaa tataatctat tgctgaaatt atctcagatg ttaagatttt cttaaagtaa    2520
attctttcaa attttagcta aaagtcttgt aataactaaa gaataataca caatctcgac    2580
cacggaaaaa aaacacataa taaatttgaa tttcgaccgc ggtacccgga attcgagctc    2640
ggtacccggg gatcttcccg atctagtaac atagatgaca ccgcgcgcga taatttatcc    2700
tagtttgcgc gctatatttt gttttctatc gcgtattaaa tgtataattg cgggactcta    2760
atcataaaaa cccatctcat aaataacgtc atgcattaca tgttaattat tacatgctta    2820
acgtaattca acagaaatta tatgataatc atcgcaagac cggcaacagg attcaatctt    2880
aagaaacttt attgccaaat gtttgaacga tctgcttcgg atcctctaga gccggaaagt    2940
gaaattgacc gatcagagtt tgaagaaaaa tttattacac actttatgta aagctgaaaa    3000
aaacggcctc cgcaggaagc cgttttttc gttatctgat ttttgtaaag gtctgataat    3060
ggtccgttgt tttgtaaatc agccagtcgc ttgagtaaaa aatccggtct gaatttctga    3120
agcctgatgt atagttaata tccgcttcac gccatgttcg tccgcttttg cccgggagtt    3180
tgccttccct gtttgagaag atgtctccgc cgatgctttt ccccggagcg acgtctgcaa    3240
ggttcccttt tgatgccacc cagccgaggg cttgtgcttc tgattttgta atgtaattat    3300
caggtagctt atgatatgtc tgaagataat ccgcaacccc gtcaaacgtg ttgataaccg    3360
gtaccatggt agctaatttc tttaagtaaa aactttgatt tgagtgatga tgttgtactg    3420
ttacacttgc accacaaggg catatataga gcacaagaca tacacaacaa cttgcaaaac    3480
taacttttgt tggagcattt cgaggaaaat ggggagtagc aggctaatct gagggtaaca    3540
ttaaggtttc atgtattaat ttgttgcaaa catggactta gtgtgaggaa aaagtaccaa    3600
aattttgtct caccctgatt tcagttatgg aaattacatt atgaagctgt gctagagaag    3660
atgtttattc tagtccagcc acccaccta tgcaagtctg cttttagctt gattcaaaaa    3720
ctgatttaat ttacattgct aaatgtgcat acttcgagcc tatgtcgctt taattcgagt    3780
aggatgtata tattagtaca taaaaaatca tgtttgaatc atctttcata aagtgacaag    3840
tcaattgtcc cttcttgttt ggcactatat tcaatctgtt aatgcaaatt atccagttat    3900
acttagctag atatccaatt ttgaataaaa atagctcttg attagtaaac cggatagtga    3960
caaagtcaca tatccatcaa acttctggtg ctcgtggcta agttctgatc gacatggggt    4020
taaaatttaa attgggacac ataaatagcc tatttgtgca aatctcccca tcgaaaatga    4080
cagattgtta catggaaaac aaaaagtcct ctgatagaag tcgcaaagta tcacaatttt    4140
ctatcgagag atagattgaa agaagtgcag ggaagcggtt aactggaaca taacacaatg    4200
tctaaattaa ttgcattcgc taaccaaaaa gtgtattact ctctccggtc cacaataagt    4260
tattttttgg ccctttttt atggtccaaa ataagtgagt tttttagatt caaaaatga    4320 tttaattatt tttttactac agtgcccttg gagtaaatgg tgttggagta tgtgttagaa    4380
atgtttatgt gaagaaatag taaaggttaa tatgatcaat ttcattgcta tttaatgtta    4440
aaatgtgaat ttcttaatct gtgtgaaaac aaccaaaaaa tcacttattg tggaccggag    4500
aaagtatata aatatatatt tggaagcgac taaaaataaa cttttctcat attatacgaa    4560
cctaaaaaca gcatatggta gtttctaggg aatctaaatc actaaaatta ataaaagaag    4620
caacaagtat caatacatat gatttacacc gtcaaacacg aaattcgtaa atatttaata    4680
```

-continued

```
taataaagaa ttaatccaaa tagcctccca ccctataact taaactaaaa ataaccagcg      4740
aatgtatatt atatgcataa tttatatatt aaatgtgtat aatcatgtat aatcaatgta      4800
taatctatgt atatggttag aaaaagtaaa caattaatat agccggctat ttgtgtaaaa      4860
atccctaata taatcgcgac ggatccccgg gaattccggg gaagcttaga tccatggagc      4920
catttacaat tgaatatatc ctgccg                                           4946
```

<210> SEQ ID NO 2
<211> LENGTH: 6548
<212> TYPE: DNA
<213> ORGANISM: Artificial Sequence
<220> FEATURE:
<223> OTHER INFORMATION: Description of Artificial Sequence: plasmid
      PTS172
<220> FEATURE:
<221> NAME/KEY: misc_feature
<222> LOCATION: Complement((2019)..(2288))
<223> OTHER INFORMATION: 3' nos: 3' untranslated region containing the
      polyadenylation signal of the nopaline synthase
      gene of Agrobacterium T-DNA.
<220> FEATURE:
<221> NAME/KEY: misc_feature
<222> LOCATION: Complement((2289)..(2624))
<223> OTHER INFORMATION: barnase: region coding for barnase
<220> FEATURE:
<221> NAME/KEY: misc_feature
<222> LOCATION: Complement((2625)..(4313))
<223> OTHER INFORMATION: PE1: promoter region of E1 gene of rice
<220> FEATURE:
<221> NAME/KEY: misc_feature
<222> LOCATION: (4336)..(5170)
<223> OTHER INFORMATION: P35S: 35S promoter region of Cauliflower Mosaic
      Virus
<220> FEATURE:
<221> NAME/KEY: misc_feature
<222> LOCATION: Complement((5711)..(6262))
<223> OTHER INFORMATION: bar: region coding for phosphinotricin
      acetyltransferase
<220> FEATURE:
<221> NAME/KEY: misc_feature
<222> LOCATION: (6263)..(6496)
<223> OTHER INFORMATION: 3'g7: 3' untranslated region containing the
      polyadenylation signal of gene 7 of Agrobacterium
      T-DNA

<400> SEQUENCE: 2

```
aattcaagct tgacgtcagg tggcactttt cggggaaatg tgcgcggaac ccctatttgt        60
ttatttttct aaatacattc aaatatgtat ccgctcatga gacaataacc ctgataaatg       120
cttcaataat attgaaaaag gaagagtatg agtattcaac atttccgtgt cgcccttatt       180 ccctttttg cggcattttg ccttcctgtt tttgctcacc cagaaacgct ggtgaaagta       240
aaagatgctg aagatcagtt gggtgcacga gtgggttaca tcgaactgga tctcaacagc       300
ggtaagatcc ttgagagttt tcgccccgaa gaacgttttc caatgatgag cacttttaaa      360
gttctgctat gtggcgcggt attatcccgt attgacgccg ggcaagagca actcggtcgc       420
cgcatacact attctcagaa tgacttggtt gagtactcac cagtcacaga aaagcatctt       480
acggatggca tgacagtaag agaattatgc agtgctgcca taaccatgag tgataacact       540
gcggccaact tacttctgac aacgatcgga ggaccgaagg agctaaccgc ttttttgcac       600
aacatggggg atcatgtaac tcgccttgat cgttgggaac cggagctgaa tgaagccata       660
ccaaacgacg agcgtgacac cacgatgcct gtagcaatgg caacaacgtt gcgcaaacta       720
ttaactggcg aactacttac tctagcttcc cggcaacaat taatagactg gatggaggcg       780
gataaagttg caggaccact tctgcgctcg gcccttccgg ctggctggtt tattgctgat       840
```

-continued

```
aaatctggag ccggtgagcg tgggtctcgc ggtatcattg cagcactggg gccagatggt      900
aagccctccc gtatcgtagt tatctacacg acggggagtc aggcaactat ggatgaacga      960
aatagacaga tcgctgagat aggtgcctca ctgattaagc attggtaact gtcagaccaa     1020
gtttactcat atatacttta gattgattta aacttcatt tttaatttaa aaggatctag      1080
gtgaagatcc ttttggctc gagtctcatg accaaaatcc cttaacgtga gttttcgttc      1140
cactgagcgt cagaccccgt agaaaagatc aaggatctt cttgagatcc ttttttttctg     1200 cgcgtaatct gctgcttgca acaaaaaaaa ccaccgctac cagcggtggt ttgtttgccg     1260
gatcaagagc taccaactct ttttccgaag gtaactggct tcagcagagc gcagatacca     1320
aatactgtcc ttctagtgta gccgtagtta ggccaccact tcaagaactc tgtagcaccg     1380
cctacatacc tcgctctgct aatcctgtta ccagtggctg ctgccagtgg cgataagtcg     1440
tgtcttaccg ggttggactc aagacgatag ttaccggata aggcgcagcg gtcgggctga     1500
acggggggtt cgtgcacaca gcccagcttg gagcgaacga cctacaccga actgagatac     1560
ctacagcgtg agcattgaga aagcgccacg cttcccgaag ggagaaaggc ggacaggtat     1620
ccggtaagcg gcagggtcgg aacaggagag cgcacgaggg agcttccagg gggaaacgcc     1680
tggtatcttt atagtcctgt cgggtttcgc cacctctgac ttgagcgtcg attttgtga     1740 tgctcgtcag gggggcggag cctatggaaa aacgccagca acgcggcctt tttacggttc     1800 ctggccttt gctggccttt tgctcacatg ttctttcctg cgttatcccc tgattctgtg     1860
gataaccgta ttaccgcctt tgagtgagct gataccgctc gccgcagccg aacgaccgag     1920
cgcagcgagt cagtgagcga ggaagcggaa gagcgcccaa tacgcaaacc gcctctcccc     1980
gcgcgttggc ctgatcagaa ttcatatgca cgtgttcccg atctagtaac atagatgaca     2040
ccgcgcgcga taatttatcc tagtttgcgc gctatatttt gttttctatc gcgtattaaa     2100
tgtataattg cgggactcta atcataaaaa cccatctcat aaataacgtc atgcattaca     2160
tgttaattat tacatgctta acgtaattca acagaaatta tatgataatc atcgcaagac     2220
cggcaacagg attcaatctt aagaaacttt attgccaaat gtttgaacga tctgcttcgg     2280
aggttacctt atctgatttt tgtaaaggtc tgataatggt ccgttgtttt gtaaatcagc     2340
cagtcgcttg agtaaagaat ccggtctgaa tttctgaagc ctgatgtata gttaatatcc     2400
gcttcacgcc atgttcgtcc gcttttgccc gggagtttgc cttccctgtt tgagaagatg     2460
tctccgccga tgcttttccc cggagcgacg tctgcaaggt tccctttga tgccaccag     2520 ccgagggctt gtgcttctga ttttgtaatg taattatcag gtagcttatg atatgtctga     2580
agataatccg caaccccgtc aaacgtgttg ataaccggta ccatcgcgac ggcttgatgg     2640
atctcttgct ggacaccggg atgctaggat gggttatcgt ggccggcgtg cgtgtgtggc     2700
ttttgtaggc gccggcgacg gcgggggcaa tgtggcaggt gagtcacggt gcaagcgtgc     2760
gcaagtgact gcaacaacca aggacggtca tggcgaaagc acctcacgcg tccaccgtct     2820
acaggatgta gcagtagcac ggtgaaagaa gtgttgtccc gtccattagg tgcattctca     2880
ccgttggcca gaacaggacc gttcaacagt taggttgagt gtaggacttt tacgtggtta     2940
atgtatggca aatagtagta aattttgccc ccattggtct ggctgagata gaacatattc     3000
tggaaagcct ctagcatatc tttttttgaca gctaaacttt gcttcttgcc ttcttggtct     3060
agcaatgacg ttgcccatgt cgtggcaaac atctggtaag gtaactgtat tcgtttgttc     3120
ccttcaacgg ctcaatcccc acaggccaag ctatccttc cttggcagta taggctcctg     3180
gagagattat actaccattt ttaagtgctt ataaagacga tgctctctaa ccagatcgat     3240
```

```
cagaaacaca aagttttagc agcgtaatat cccacacaca tacacacacg aagctatgcc    3300
tcctcatttt ccgagagatt ctgacagtga ccagaatgtc agaatgccat ttcatgggca    3360
caagtcgatc cacaagcttc ttggtggagg tcaaggtgtg ctattattat tcgctttcta    3420
ggaaattatt cagaattagt gccttttatc ataacttctc tctgagccga tgtggttttg    3480
gatttcattg ttgggagcta tgcagttgcg atattctgc tgtggaagaa caggaactta     3540
tctgcggggg tccttgctgg ggcaacattg atatggttcc tgttcgatgt agtagaatac    3600
aatataattc cgctcctttg ccagattgcc attcttgcca tgcttgtgat cttcatttgg    3660
tcaaatgccg caccactctt ggacaggtat tagctttatt tcctgtggag atggtagaaa    3720
actcagctta cagaaatggc atttcacgta gtataacgca agacattagg tactaaaact    3780
caactaactg tttccgaatt tcagggcccc tccaaggatc ccagaaatca tcatctctga    3840
acatgccttc agagaaatgg cattgaccgt ccattacaaa ctaacgtaca ctgtatctgt    3900
tctttacgac attgcatgtg gaaaggatct gaagagattt ctcctggtac ataataatct    3960
actcctttgc tacgttaata agagatgtaa aaacatgcaa cagttccagt gccaacattg    4020
tccaaggatt gtgcaattct ttctggagcg ctaaaattga ccagattaga cgcatcagaa    4080
tattgaattg cagagttagc caataatcct cataatgtta atgtgctatt gttgttcact    4140
actcaatata gttctggact aacaatcaga ttgtttatga tattaaggtg gttggatctc    4200
tattggtatt gtcggcgatt ggaagttctt gcagcttgac aagtctacta tatattggta    4260
ggtattccag ataaatatta aattttaata aaacaatcac acagaaggat ctgcggccgc    4320
tagcctaggc ccgggcccac aaaaatctga gcttaacagc acagttgctc ctctcagagc    4380
agaatcgggt attcaacacc ctcatatcaa ctactacgtt gtgtataacg gtccacatgc    4440
cggtatatac gatgactggg gttgtacaaa ggcggcaaca aacggcgttc ccggagttgc    4500
acacaagaaa tttgccacta ttacagaggc aagagcagca gctgacgcgt acacaacaag    4560
tcagcaaaca gacaggttga acttcatccc caaaggagaa gctcaactca gcccaagag    4620 ctttgctaag gccctaacaa gcccaccaaa gcaaaaagcc cactggctca cgctaggaac    4680
caaaaggccc agcagtgatc cagccccaaa agagatctcc tttgcccgg agattacaat    4740 ggacgatttc ctctatcttt acgatctagg aaggaagttc gaaggtgaag gtgacgacac    4800
tatgttcacc actgataatg agaaggttag cctcttcaat ttcagaaaga atgctgaccc    4860
acagatggtt agagaggcct acgcagcagg tctcatcaag acgatctacc cgagtaacaa    4920
tctccaggag atcaaatacc ttcccaagaa ggttaaagat gcagtcaaaa gattcaggac    4980
taattgcatc aagaacacag agaaagcat atttctcaag atcagaagta ctattccagt    5040
atggacgatt caaggcttgc ttcataaacc aaggcaagta atagagattg gagtctctaa    5100
aaaggtagtt cctactgaat ctaaggccat gcatggagtc taagattcaa atcgaggatc    5160
taacagaact cgccgtgaag actggcgaac agttcataca gagtcttta cgactcaatg    5220 acaagaagaa aatcttcgtc aacatggtgg agcacgacac tctggtctac tccaaaaatg    5280
tcaaagatac agtctcagaa gaccaaaggg ctattgagac ttttcaacaa aggataattt    5340
cgggaaacct cctcggattc cattgcccag ctatctgtca cttcatcgaa aggacagtag    5400
aaaaggaagg tggctcctac aaatgccatc attgcgataa aggaaaggct atcattcaag    5460
atgcctctgc cgacagtggt cccaaagatg gaccccacc cacgaggagc atcgtggaaa    5520
aagaagacgt tccaaccacg tcttcaaagc aagtggattg atgtgacatc tccactgacg    5580
```

-continued

| | |
|---|---|
| taaggyatga cgcacaatcc cactatcctt cgcaagaccc ttcctctata taaggaagtt | 5640 |
| catttcattt ggagaggaca cgctgaaatc accagtctct ctctataaat ctatctctct | 5700 |
| ctctataacc atggacccag aacgacgccc ggccgacatc cgccgtgcca ccgaggcgga | 5760 |
| catgccggcg gtctgcacca tcgtcaacca ctacatcgag acaagcacgg tcaacttccg | 5820 |
| taccgagccg caggaaccgc aggagtggac ggacgacctc gtccgtctgc gggagcgcta | 5880 |
| tccctggctc gtcgccgagg tggacggcga gtcgccggc atcgcctacg cgggcccctg | 5940 |
| gaaggcacgc aacgcctacg actggacggc cgagtcgacc gtgtacgtct cccccccgcca | 6000 |
| ccagcggacg ggactgggct ccacgctcta cacccacctg ctgaagtccc tggaggcaca | 6060 |
| gggcttcaag agcgtggtcg ctgtcatcgg gctgcccaac gacccgagcg tgcgcatgca | 6120 |
| cgaggcgctc ggatatgccc cccgcggcat gctgcgggcg gccggcttca agcacgggaa | 6180 |
| ctggcatgac gtgggtttct ggcagctgga cttcagcctg ccggtaccgc ccgtccggt | 6240 |
| cctgcccgtc accgagatct gagatcacgc gttctaggat cccccgatga gctaagctag | 6300 |
| ctatatcatc aatttatgta ttacacataa tatcgcactc agtctttcat ctacggcaat | 6360 |
| gtaccagctg atataatcag ttattgaaat atttctgaat ttaaacttgc atcaataaat | 6420 |
| ttatgttttt gcttggacta taatacctga cttgttattt tatcaataaa tatttaaact | 6480 |
| atatttcttt caagatggga attaacatct acaaattgcc ttttcttatc gaccatgtac | 6540 |
| gtatcgcg | 6548 |

```
<210> SEQ ID NO 3
<211> LENGTH: 1601
<212> TYPE: DNA
<213> ORGANISM: Artificial Sequence
<220> FEATURE:
<223> OTHER INFORMATION: Description of Artificial Sequence: T72
      promoter region
<220> FEATURE:
<221> NAME/KEY: misc_feature
<222> LOCATION: (1)..(1601)
<223> OTHER INFORMATION: promoter region of T72 gene of rice

<400> SEQUENCE: 3
```

| | |
|---|---|
| cgccgtgagt gtcttctgcc gccgaggggc tctcgctcgt cgtcgatgcc tgcacggtgc | 60 |
| gtgcgtgtgt gtcgtggtgg tggtggcgat acgcgacgcg agctcgattt ataggagggg | 120 |
| atcgaaggag gggagcgcgc gcggcgaggc ccgcgttgct cacctacgcc gcgcgcatgc | 180 |
| ggcggacgcg cggtcggcgc ccgcgccggc cgggaggacg agggcgcaag cgtgtgagcc | 240 |
| accgaacgcg cgcgcgcgcc gcggcgcgaa ctctccatcg cgtcgcggcg agccgagagc | 300 |
| cgacgagagc gtttcgcgcg cgcggttggg ccggcgacaa gatgggccgt agccctgggc | 360 |
| ctcgtgccat cttttttttt cttttttgcc tttttggcc tggcaatttc tttttgtttt | 420 |
| tagtcttttt gtggtgataa tgtgtcgtct tccggtgaac taatttactc gttgatcttt | 480 |
| ttgtgtccct tcgaatattc gcagtggtag aagatgacta ctactaccag tagttgatct | 540 |
| cgaatggcaa cttttgtgca gaacttattc cacggctatg tcagcttcca ctgtgactaa | 600 |
| aaaaactacg gccatctttt ggacttgttc tatcttggaa ctgaacaaaa aggacgatcc | 660 |
| tgatgtacac acgcatagt ttccagcact ggatgccaag ttgccaactg ttaccacgat | 720 |
| aatgaacga cgagatgaga tattatacaa gtccaatgga tcaagatcct gtgcagttgt | 780 |
| tattgtaact gtaacttaag ccgttaacat gtacatcaca tttcctactc tatcaatgtc | 840 |
| ttgtgcgggt tgtttcaaaa aaacatgtac atcacatgat ctagaacgga aggccaggat | 900 |

-continued

```
atgaagtggt actgcagcaa aaacactgta gcagagatgt actattatgc atgtactgta      960
gcagtcatct agagccgttg gatctgaaaa cgaatggaca tgattgtgtg cagttgctat     1020
tgtgcagtta caatagcaac tgcatttgat cttaatccaa gtccaataca tgcagaacag     1080
tagctacgag ctggaaagga tgcaaatctg ggtgacactg acagcaaccg tggaagaaca     1140
acagcagcaa agtcccagag ggatggcaat ttgaaggaat ttaaatactc taatattact     1200
ccacccgtta aaaaaaacaa cttgctacgc ataatatatg ttcggattta tagcgagaag     1260 ttaattttttc atgagaagaa gaatatatat gtaaatgta ctaggagagt actcgcttca     1320
taaatataaa tattcataag ttgtccagtg aagatagctt tagaaaaaac tagttatttt     1380
atttgtcaaa ttttaaattt tgaagtagtt agattatctt tctagtagtt ctgattggtt     1440
gaaaatgttt agattttcat gtgttaagag ttccgtatcc taaaaatagt aatataatt      1500 taaatcatat atatatat atatatatat atatatatat atatatatat atatatatat       1560
tgttgaacgg tttgtgctct ggttgctatc ctgttctgtg g                         1601
```

<210> SEQ ID NO 4
<211> LENGTH: 6291
<212> TYPE: DNA
<213> ORGANISM: Artificial Sequence
<220> FEATURE:
<223> OTHER INFORMATION: Description of Artificial Sequence: plasmid pVE136
<220> FEATURE:
<221> NAME/KEY: misc_feature
<222> LOCATION: Complement((425)..(687))
<223> OTHER INFORMATION: 3' nos: 3' untranslated region containing the polyadenylation signal of the nopaline synthase gene of Agrobacterium T-DNA
<220> FEATURE:
<221> NAME/KEY: misc_feature
<222> LOCATION: Complement((803)..(1138))
<223> OTHER INFORMATION: barnase: region coding for barnase
<220> FEATURE:
<221> NAME/KEY: misc_feature
<222> LOCATION: Complement((1138)..(2317))
<223> OTHER INFORMATION: PCa55: stamen-specific promoter from corn gene CA55
<220> FEATURE:
<221> NAME/KEY: misc_feature
<222> LOCATION: (2355)..(3187)
<223> OTHER INFORMATION: p35S: 35S promoter region of Cauliflower mosaic virus
<220> FEATURE:
<221> NAME/KEY: misc_feature
<222> LOCATION: (3188)..(3739)
<223> OTHER INFORMATION: bar: region coding for phosphinoacetyl transferase
<220> FEATURE:
<221> NAME/KEY: misc_feature
<222> LOCATION: (3757)..(4017)
<223> OTHER INFORMATION: 3' nos: 3' untranslated region containing the polyadenylation of the nopaline synthase gene of Agrobacterium T-DNA
<220> FEATURE:
<221> NAME/KEY: misc_feature
<222> LOCATION: (699)..(702)
<223> OTHER INFORMATION: region with unknown sequence (may contain up to 15 nucleotides)

<400> SEQUENCE: 4

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
```

-continued

| | |
|---|---|
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acccggggat | 420 |
| cttcccgatc tagtaacata gatgacaccg cgcgcgataa tttatcctag tttgcgcgct | 480 |
| atattttgtt ttctatcgcg tattaaatgt ataattgcgg gactctaatc ataaaaaccc | 540 |
| atctcataaa taacgtcatg cattacatgt taattattac atgcttaacg taattcaaca | 600 |
| gaaattatat gataatcatc gcaagaccgg caacaggatt caatcttaag aaactttatt | 660 |
| gccaaatgtt tgaacgatct gcttcggatc ctctagagnn nnccggaaag tgaaattgac | 720 |
| cgatcagagt ttgaagaaaa atttattaca cactttatgt aaagctgaaa aaaacggcct | 780 |
| ccgcaggaag ccgttttttt cgttatctga tttttgtaaa ggtctgataa tggtccgttg | 840 |
| ttttgtaaat cagccagtcg cttgagtaaa gaatccggtc tgaatttctg aagcctgatg | 900 |
| tatagttaat atccgcttca cgccatgttc gtccgctttt gcccgggagt ttgccttccc | 960 |
| tgtttgagaa gatgtctccg ccgatgcttt tccccggagc gacgtctgca aggttccctt | 1020 |
| ttgatgccac ccagccgagg gcttgtgctt ctgattttgt aatgtaatta tcaggtagct | 1080 |
| tatgatatgt ctgaagataa tccgcaaccc cgtcaaacgt gttgataacc ggtaccatgg | 1140 |
| ctgcagctag ttagctcgat gtatcttctg tatatgcagt gcagcttctg cgttttggct | 1200 |
| gctttgagct gtgaaatctc gcttccagt ccctgcgtgt tttatagtgc tgtacgttcg | 1260 |
| tgatcgtgag caaacagggc gtgcctcaac tactggtttg gttgggtgac aggcgccaac | 1320 |
| tacgtgctcg taaccgatcg agtgagcgta atgcaacatt ttttcttctt ctctcgcatt | 1380 |
| ggtttcatcc agccaggaga cccgaatcga attgaaatca caaatctgag gtacagtatt | 1440 |
| tttacagtac cgttcgttcg aaggtcttcg acaggtcaag gtaacaaaat cagttttaaa | 1500 |
| ttgttgtttc agatcaaaga aaattgagat gatctgaagg acttggacct tcgtccaatg | 1560 |
| aaacacttgg actaattaga ggtgaattga agcaagcag atgcaaccga aggtggtgaa | 1620 |
| agtggagttt cagcattgac gacgaaaacc ttcgaacggt ataaaaaga agccgcaatt | 1680 |
| aaacgaagat ttgccaaaaa gatgcatcaa ccaagggaag acgtgcatac atgtttgatg | 1740 |
| aaaactcgta aaaactgaag tacgattccc cattcccctc cttttctcgt ttcttttaac | 1800 |
| tgaagcaaag aatttgtatg tattccctcc attccatatt ctaggaggtt ttggcttttc | 1860 |
| ataccctcct ccatttcaaa ttatttgtca tacattgaag atatacacca ttctaattta | 1920 |
| tactaaatta cagcttttag atacatatat tttattatac acttagatac gtattatata | 1980 |
| aaacacctaa tttaaaataa aaattatat aaaaagtgta tctaaaaaat caaaatacga | 2040 |
| cataatttga aacggagggg tactacttat gcaaaccaat cgtggtaacc ctaaacccta | 2100 |
| tatgaatgag gccatgattg taatgcaccg tctgattaac caagatatca atggtcaaag | 2160 |
| atatacatga tacatccaag tcacagcgaa ggcaaatgtg acaacagttt tttttaccag | 2220 |
| agggacaagg gagaatatct attcagatgt caagttcccg tatcacactg ccaggtcctt | 2280 |
| actccagacc atcttccggc tctattgatg cataccagga attgatctag agtcgacctg | 2340 |
| caggcatgca agctcctacg cagcaggtct catcaagacg atctacccga gtaacaatct | 2400 |
| ccaggagatc aaataccttc ccaagaaggt taaagatgca gtcaaaagat tcaggactaa | 2460 |
| ttgcatcaag aacacagaga aagacatatt tctcaagatc agaagtacta ttccagtatg | 2520 |
| gacgattcaa ggcttgcttc ataaaccaag gcaagtaata gagattggag tctctaaaaa | 2580 |
| ggtagttcct actgaatcta aggccatgca tggagtctaa gattcaaatc gaggatctaa | 2640 |

```
cagaactcgc cgtgaagact ggcgaacagt tcatacagag tcttttacga ctcaatgaca    2700
agaagaaaat cttcgtcaac atggtggagc acgacactct ggtctactcc aaaaatgtca    2760
aagatacagt ctcagaagac caaagggcta ttgagacttt tcaacaaagg ataatttcgg    2820
gaaacctcct cggattccat tgcccagcta tctgtcactt catcgaaagg acagtagaaa    2880
aggaaggtgg ctcctacaaa tgccatcatt gcgataaagg aaaggctatc attcaagatg    2940
cctctgccga cagtggtccc aaagatggac cccacccac gaggagcatc gtggaaaaag    3000
aagacgttcc aaccacgtct tcaaagcaag tggattgatg tgacatctcc actgacgtaa    3060
gggatgacgc acaatcccac tatccttcgc aagacccttc ctctatataa ggaagttcat    3120
ttcatttgga gaggacacgc tgaaatcacc agtctctctc tataaatcta tctctctctc    3180
tataaccatg gacccagaac gacgcccggc cgacatccgc cgtgccaccg aggcggacat    3240
gccggcggtc tgcaccatcg tcaaccacta catcgagaca agcacggtca acttccgtac    3300
cgagccgcag gaaccgcagg agtggacgga cgacctcgtc cgtctgcggg agcgctatcc    3360
ctggctcgtc gccgaggtgg acggcgaggt cgccggcatc gcctacgcgg gccctggaa    3420 ggcacgcaac gcctacgact ggacggccga gtcgaccgtg tacgtctccc ccgccacca    3480 gcggacggga ctgggctcca cgctctacac ccacctgctg aagtccctgg aggcacaggg    3540
cttcaagagc gtggtcgctg tcatcgggct gcccaacgac ccgagcgtgc gcatgcacga    3600
ggcgctcgga tatgccccc gcggcatgct cgggcggcc ggcttcaagc acgggaactg    3660
gcatgacgtg ggtttctggc agctggactt cagcctgccg gtaccgcccc gtccggtcct    3720
gcccgtcacc gagatctgat ctcacgcgtc taggatccga agcagatcgt tcaaacattt    3780
ggcaataaag tttcttaaga ttgaatcctg ttgccggtct tgcgatgatt atcatataat    3840
ttctgttgaa ttacgttaag catgtaataa ttaacatgta atgcatgacg ttatttatga    3900
gatgggtttt tatgattaga gtcccgcaat tatacattta atacgcgata gaaaacaaaa    3960
tatagcgcgc aaactaggat aaattatcgc gcgcggtgtc atctatgtta ctagatcggg    4020
aagatcctct agagtcgacc tgcaggcatg caagcttggc gtaatcatgg tcatagctgt    4080
ttcctgtgtg aaattgttat ccgctcacaa ttccacacaa catacgagcc ggaagcataa    4140
agtgtaaagc ctggggtgcc taatgagtga gctaactcac attaattgcg ttgcgctcac    4200
tgcccgcttt ccagtcggga aacctgtcgt gccagctgca ttaatgaatc ggccaacgcg    4260
cggggagagg cggtttgcgt attgggcgct cttccgcttc ctcgctcact gactcgctgc    4320
gctcggtcgt tcggctgcgg cgagcggtat cagctcactc aaaggcggta atacggttat    4380
ccacagaatc agggg ataac gcaggaaaga acatgtgagc aaaaggccag caaaaggcca    4440
ggaaccgtaa aaaggccgcg ttgctggcgt ttttccatag gctccgcccc cctgacgagc    4500
atcacaaaaa tcgacgctca agtcagaggt ggcgaaaccc gacaggacta taaagatacc    4560
aggcgtttcc ccctggaagc tccctcgtgc gctctcctgt ccgaccctg ccgcttaccg    4620 gatacctgtc gcctttctc ccttcgggaa gcgtggcgct ttctcaatgc tcacgctgta    4680
ggtatctcag ttcggtgtag tcgttcgct ccaagctggg ctgtgtgcac gaacccccg    4740 ttcagcccga ccgctgcgcc ttatccgta actatcgtct tgagtccaac ccggtaagac    4800
acgacttatc gccactggca gcagccactg gtaacaggat tagcagagcg aggtatgtag    4860
gcggtgctac agagttcttg aagtggtggc ctaactacgg ctacactaga aggacagtat    4920
ttggtatctg cgctctgctg aagccagtta ccttcggaaa aagagttggt agctcttgat    4980
```

```
ccggcaaaca aaccaccgct ggtagcggtg gttttttttgt ttgcaagcag cagattacgc      5040
gcagaaaaaa aggatctcaa gaagatcctt tgatcttttc tacggggtct gacgctcagt      5100
ggaacgaaaa ctcacgttaa gggattttgg tcatgagatt atcaaaaagg atcttcacct      5160
agatcctttt aaattaaaaa tgaagtttta atcaatcta aagtatatat gagtaaactt       5220
ggtctgacag ttaccaatgc ttaatcagtg aggcacctat ctcagcgatc tgtctatttc      5280
gttcatccat agttgcctga ctccccgtcg tgtagataac tacgatacgg gagggcttac      5340
catctggccc cagtgctgca atgataccgc gagacccacg ctcaccggct ccagatttat      5400
cagcaataaa ccagccagcc ggaagggccg agcgcagaag tggtcctgca actttatccg      5460
cctccatcca gtctattaat tgttgccggg aagctagagt aagtagttcg ccagttaata      5520
gtttgcgcaa cgttgttgcc attgctacag gcatcgtggt gtcacgctcg tcgtttggta      5580
tggcttcatt cagctccggt tcccaacgat caaggcgagt tacatgatcc cccatgttgt      5640
gcaaaaaagc ggttagctcc ttcggtcctc cgatcgttgt cagaagtaag ttggccgcag      5700
tgttatcact catggttatg gcagcactgc ataattctct tactgtcatg ccatccgtaa      5760
gatgcttttc tgtgactggt gagtactcaa ccaagtcatt ctgagaatag tgtatgcggc      5820
gaccgagttg ctcttgcccg gcgtcaatac gggataatac cgcgccacat agcagaactt      5880
taaaagtgct catcattgga aaacgttctt cggggcgaaa actctcaagg atcttaccgc      5940
tgttgagatc cagttcgatg taacccactc gtgcacccaa ctgatcttca gcatctttta      6000
ctttcaccag cgtttctggg tgagcaaaaa caggaaggca aaatgccgca aaaagggaa       6060 taagggcgac acggaaatgt tgaatactca tactcttcct ttttcaatat tattgaagca      6120
tttatcaggg ttattgtctc atgagcggat acatatttga atgtatttag aaaaataaac      6180
aaataggggt tccgcgcaca tttccccgaa aagtgccacc tgacgtctaa gaaaccatta      6240
ttatcatgac attaacctat aaaaataggc gtatcacgag gccctttcgt c              6291
```

<210> SEQ ID NO 5
<211> LENGTH: 5560
<212> TYPE: DNA
<213> ORGANISM: Artificial Sequence
<220> FEATURE:
<223> OTHER INFORMATION: Description of Artificial Sequence: T-DNA of
      plasmid pTHW142
<220> FEATURE:
<221> NAME/KEY: misc_feature
<222> LOCATION: (1)..(25)
<223> OTHER INFORMATION: RB: right border sequence of octopine TL-DNA
      from pTiB6S3
<220> FEATURE:
<221> NAME/KEY: misc_feature
<222> LOCATION: (84)..(296)
<223> OTHER INFORMATION: 3' g7: 3' untranslated region containing the
      polyadenylation signal of gene 7 of Agrobacterium
      T-DNA
<220> FEATURE:
<221> NAME/KEY: misc_feature
<222> LOCATION: (318)..(869)
<223> OTHER INFORMATION: bar: region coding for phosphinotricin
      acetyltransferase
<220> FEATURE:
<221> NAME/KEY: misc_feature
<222> LOCATION: (830)..(2760)
<223> OTHER INFORMATION: pSSU: promoter region of Rubisco small subunit
      gene of Arabidopsis thaliana
<220> FEATURE:
<221> NAME/KEY: misc_feature
<222> LOCATION: (2765)..(3058)
<223> OTHER INFORMATION: 3' untranslated region of the CaMV 35S
      transcript containing polyadenylation signals
<220> FEATURE:

<221> NAME/KEY: misc_feature
<222> LOCATION: (3059)..(5056)
<223> OTHER INFORMATION: uidA: region coding for beta-glucuronidase
<220> FEATURE:
<221> NAME/KEY: misc_feature
<222> LOCATION: (4483)..(4671)
<223> OTHER INFORMATION: IV2: region corresponding to the second intron of the ST-LS1 gene
<220> FEATURE:
<221> NAME/KEY: misc_feature
<222> LOCATION: (5067)..(5502)
<223> OTHER INFORMATION: P35S: 35S promoter region of CaMV
<220> FEATURE:
<221> NAME/KEY: misc_feature
<222> LOCATION: (5533)..(5560)
<223> OTHER INFORMATION: LB: left border sequence of octopine TL-DNA from pTIB6S3
<220> FEATURE:
<221> NAME/KEY: misc_feature
<222> LOCATION: (5058)..(5059)
<223> OTHER INFORMATION: region with unknown sequence (may contain up to 20 nucleotides)
<220> FEATURE:
<221> NAME/KEY: misc_feature
<222> LOCATION: (5077)..(5078)
<223> OTHER INFORMATION: region with unknown sequence (may contain up to 20 nucleotides)
<220> FEATURE:
<221> NAME/KEY: misc_feature
<222> LOCATION: (5476)..(5479)
<223> OTHER INFORMATION: region with unknown sequence (may contain up to 20 nucleotides)

<400> SEQUENCE: 5

```
aattcaacg gtatatatcc tgccagtact cggccgtcga gtacatggtc gataagaaaa      60
ggcaatttgt agatgttaat tcccatcttg aaagaaatat agtttaaata tttattgata    120
aaataacaag tcaggtatta tagtccaagc aaaaacataa atttattgat gcaagtttaa    180
attcagaaat atttcaataa ctgattatat cagctggtac attgccgtag atgaaagact    240
gagtgcgata ttatgtgtaa tacataaatt gatgatatag ctagcttagc tcatcggggg    300
atcctagacg cgtgagatca gatctcggtg acgggcagga ccgacggggg cggtaccggc    360
aggctgaagt ccagctgcca gaaacccacg tcatgccagt tcccgtgctt gaagccggcc    420
gcccgcagca tgccgcgggg ggcatatccg agcgcctcgt gcatgcgcac gctcgggtcg    480
ttgggcagcc cgatgacagc gaccacgctc ttgaagccct gtgcctccag ggacttcagc    540
aggtgggtgt agagcgtgga gcccagtccc gtccgctggt ggcgggggga gacgtacacg    600
gtcgactcgg ccgtccagtc gtaggcgttg cgtgccttcc aggggcccgc gtaggcgatg    660
ccggcgacct cgccgtccac ctcggcgacg agccagggat agcgctcccg cagacggacg    720
aggtcgtccg tccactcctg cggttcctgc ggctcggtac ggaagttgac cgtgcttgtc    780
tcgatgtagt ggttgacgat ggtgcagacc gccggcatgt ccgcctcggt ggcacggcgg    840
atgtcggccg ggcgtcgttc tgggtccatg cagttaactc ttccgccgtt gcttgtgatg    900
gaagtaatgt cgttgttagc cttgcgggtg gctgggaagg cagcggagga cttaagtccg    960
ttgaaaggag cgaccatagt ggcctgagcc ggagaggcaa ccatagtagc ggaagagagc   1020
atagaggaag ccattgttct tctttactct ttgtgtgact gaggtttggt ctagtgcttt   1080
ggtcatctat atataatgat aacaacaatg agaacaagct ttggagtgat cggagggtct   1140
aggatacatg agattcaagt ggactaggat ctacaccgtt ggattttgag tgtggatatg   1200
tgtgaggtta attttacttg gtaacggcca caaaggccta aggagaggtg ttgagaccct   1260
tatcggcttg aaccgctgga ataatgccac gtggaagata attccatgaa tcttatcgtt   1320
```

-continued

```
atctatgagt gaaattgtgt gatggtggag tggtgcttgc tcattttact tgcctggtgg      1380
acttggccct ttccttatgg ggaatttata ttttacttac tatagagctt tcatacctt       1440 tttttacctt ggatttagtt aatatataat ggtatgattc atgaataaaa atgggaaatt      1500
tttgaatttg tactgctaaa tgcataagat taggtgaaac tgtggaatat atattttttt      1560
catttaaaag caaaatttgc cttttactag aattataaat atagaaaaat ataacatt        1620 caaataaaaa tgaaaataag aactttcaaa aaacagaact atgtttaatg tgtaaagatt      1680
agtcgcacat caagtcatct gttacaatat gttacaacaa gtcataagcc caacaaagtt     1740
agcacgtcta aataaactaa agagtccacg aaaatattac aaatcataag cccaacaaag     1800
ttattgatca aaaaaaaaaa acgcccaaca aagctaaaca aagtccaaaa aaaacttctc     1860
aagtctccat cttcctttat gaacattgaa aactatacac aaaacaagtc agataaatct    1920
ctttctgggc ctgtcttccc aacctcctac atcacttccc tatcggattg aatgttttac    1980
ttgtaccttt tccgttgcaa tgatattgat agtatgtttg tgaaaactaa tagggttaac    2040
aatcgaagtc atggaatatg gatttggtcc aagattttcc gagagctttc tagtagaaag    2100
cccatcacca gaaatttact agtaaaataa atcaccaatt aggtttctta ttatgtgcca    2160
aattcaatat aattatagag gatatttcaa atgaaaacgt atgaatgtta ttagtaaatg    2220
gtcaggtaag acattaaaaa aatcctacgt cagatattca actttaaaaa ttcgatcagt    2280
gtggaattgt acaaaaattt gggatctact atatatatat aatgctttac aacacttgga    2340 ttttttttttg gaggctggaa tttttaatct acatatttgt tttggccatg caccaactca    2400
ttgtttagtg taatactttg attttgtcaa atatatgtgt tcgtgtatat ttgtataaga    2460
atttctttga ccatatacac acacacatat atatatatat atatatatta tatatcatgc    2520
acttttaatt gaaaaaataa tatatatata tatagtgcat ttttttctaac aaccatatat    2580 gttgcgattg atctgcaaaa atactgctag agtaatgaaa aatataatct attgctgaaa    2640
ttatctcaga tgttaagatt ttcttaaagt aaattctttc aaattttagc taaaagtctt    2700
gtaataacta aagaataata cacaatctcg accacggaaa aaaacacat aataaatttg     2760 aattagcttg catgcctgca ggtcactgga ttttggtttt aggaattaga aattttattg    2820
atagaagtat tttacaaata caaatacata ctaagggttt cttatatgct caacacatga    2880
gcgaaacctt ataagaaccc taattccctt atctgggaac tactcacaca ttattctgga    2940
gaaaaataga gagagataga tttgtagaga gagactggtg attttttgcgc cgggtaccga    3000 gctcggtagc aattcccgag gctgtagccg acgatggtgc gccaggagag ttgttgattc    3060
attgtttgcc tccctgctgc ggttttttcac cgaagttcat gccagtccag cgttttttgca    3120 gcagaaaagc cgccgacttc ggtttgcggt cgcgagtgaa gatccctttc ttgttaccgc    3180
caacgcgcaa tatgccttgc gaggtcgcaa aatcggcgaa attccatacc tgttcaccga    3240
cgacggcgct gacgcgatca agacgcggt gatacatatc cagccatgca cactgatact    3300
cttcactcca catgtcggtg tacattgagt gcagcccggc taacgtatcc acgccgtatt    3360
cggtgatgat aatcggctga tgcagtttct cctgccaggc cagaagttct ttttccagta    3420
ccttctctgc cgtttccaaa tcgccgcttt ggacatacca tccgtaataa cggttcaggc    3480
acagcacatc aaagagatcg ctgatggtat cggtgtgagc gtcgcagaac attacattga    3540
cgcaggtgat cggacgcgtc gggtcgagtt tacgcgttgc ttccgccagt ggcgaaatat    3600
tcccgtgcac ttgcggacgg gtatccggtt cgttggcaat actccacatc accacgcttg    3660
ggtggttttt gtcacgcgct atcagctctt taatcgcctg taagtgcgct tgctgagttt    3720
```

-continued

```
ccccgttgac tgcctcttcg ctgtacagtt ctttcggctt gttgcccgct tcgaaaccaa    3780
tgcctaaaga gaggttaaag ccgacagcag cagtttcatc aatcaccacg atgccatgtt    3840
catctgccca gtcgagcatc tcttcagcgt aagggtaatg cgaggtacgg taggagttgg    3900
ccccaatcca gtccattaat gcgtggtcgt gcaccatcag cacgttatcg aatcctttgc    3960
cacgtaagtc cgcatcttca tgacgaccaa agccagtaaa gtagaacggt ttgtggttaa    4020
tcaggaactg ttcgcccttc actgccactg accggatgcc gacgcgaagc gggtagatat    4080
cacactctgt ctggcttttg gctgtgacgc acagttcata gagataacct tcacccggtt    4140
gccagaggtg cggattcacc acttgcaaag tcccgctagt gccttgtcca gttgcaacca    4200
cctgttgatc cgcatcacgc agttcaacgc tgacatcacc attggccacc acctgccagt    4260
caacagacgc gtggttacag tcttgcgcga catgcgtcac cacggtgata tcgtccaccc    4320
aggtgttcgg cgtggtgtag agcattacgc tgcgatggat tccggcatag ttaaagaaat    4380
catggaagta agactgcttt ttcttgccgt tttcgtcggt aatcaccatt cccggcggga    4440
tagtctgcca gttcagttcg ttgttcacac aaacggtgat acctgcacat caccatgttt    4500
tggtcatata ttagaaaagt tataaattaa aatatacaca cttataaact acagaaaagc    4560
aattgctata tactacattc ttttattttg aaaaaaatat ttgaaatatt atattactac    4620
taattaatga taattattat atatatatca aaggtagaag cagaaactta cgtacacttt    4680
tcccggcaat aacatacggc gtgacatcgg cttcaaatgg cgtatagccg ccctgatgct    4740
ccatcacttc ctgattattg acccacactt tgccgtaatg agtgaccgca tcgaaacgca    4800
gcacgatacg ctggcctgcc caacctttcg gtataaagac ttcgcgctga taccagacgt    4860
tgcccgcata attacgaata tctgcatcgg cgaactgatc gttaaaactg cctggcacag    4920
caattgcccg gctttcttgt aacgcgcttt cccaccaacg ctgatcaatt ccacagtttt    4980
cgcgatccag actgaatgcc cacaggccgt cgagtttttt gatttcacgg gttggggttt    5040
ctacaggacg gaccatgnnc ccggggatcc tctaganntt atagagagag agatagattt    5100
atagagagag actggtgatt tcagcgtgtc ctctccaaat gaaatgaact tccttatata    5160
gaggaagggt cttgcgaagg atagtgggat tgtgcgtcat cccttacgtc agtggagatg    5220
tcacatcaat ccacttgctt tgaagacgtg gttggaacgt cttcttttc cacgatgctc    5280
ctcgtgggtg ggggtccatc tttgggacca ctgtcggcag aggcatcttg aatgatagcc    5340
tttcctttat cgcaatgatg gcatttgtag gagccacctt cctttctac tgtcctttcg    5400
atgaagtgac agatagctgg gcaatggaat ccgaggaggt ttcccgaaat tatcctttgt    5460
tgaaaagtct caatannnng tcgacctgca ggcatgcaag ctaattccgg ggaagcttag    5520
atccatggag ccatttacaa ttgaatatat cctgccgccg                           5560
```